(12) United States Patent
Zhang et al.

(10) Patent No.: US 6,844,324 B1
(45) Date of Patent: Jan. 18, 2005

(54) MODULAR PEPTIDE MEDIATED INTRACELLULAR DELIVERY SYSTEM AND USES THEREFORE

(75) Inventors: Shuguang Zhang, Lexington, MA (US); John J. Schwartz, Newtonville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/438,905

(22) Filed: Nov. 12, 1999

(51) Int. Cl.[7] .................. A61K 48/00; C07H 21/04; C12Q 1/68
(52) U.S. Cl. .................. 514/44; 514/2; 536/24.5; 435/6
(58) Field of Search .................. 435/352, 366, 435/6, 320.1, 235.1, 69.1; 530/350; 514/2, 44; 536/23.1, 24.5, 23.5

(56) References Cited

U.S. PATENT DOCUMENTS

| | | | | |
|---|---|---|---|---|
| 5,714,353 A | * | 2/1998 | Pathak et al. | |
| 5,877,282 A | * | 3/1999 | Nadler et al. | ............... 530/350 |
| 5,929,042 A | * | 7/1999 | Troy et al. | ............... 514/44 |
| 5,981,273 A | * | 11/1999 | Curiel et al. | ............. 435/320.1 |
| 6,080,724 A | * | 6/2000 | Chassaing et al. | |

OTHER PUBLICATIONS

Schofield et al, British Med. Bull, vol. 51, No. 1, pp. 56–71, 1995.*
Crooke, S.T., Antisense Research and Application, Chapter 1, pp. 1–50, published by Springer–Verlag, 1998.*
Branch, A.D., Trends in Biochem. Sci. (TIBS), vol. 23, pp. 45–50, 1998.*
Crystal, R.G., Science, vol. 270, pp. 404–410, 1995.*
Verma et al, Nature, vol. 389, pp. 239–242, 1997.*
Friedmannj, T., Scientific American, Jun. vol., pp. 96–101, 1997.*
Schwartz and Zhang Peptide mediated cellular delivery. Current Opinion in Molecular Therapeutics. Feb. 2000 2(2) p 162 167.*
Adam, S., "Transport pathways of macromolecules between the nucleus and the cytoplasm," *Current Opinion in Cell Biology,* 11:402–406 (1999).
Albini, A., et al., "Antiogenic properties of human immunodeficiency virus type 1 Tat protein," Proc. Natl. Acad. Sci. USA, 92:4838–4842 (1995).
Aldrian–Herrada, G., et al., "A peptide nucleic acid (PNA) is more rapidly internalized in cultured neurons when coupled to a retro–inverso delivery peptide. The antisense activity depresses the target mRNA and protein in magnocellular oxytocin neurons," *Nucl. Acid Res.,* 26:4910–4916 (1998).
Anderson W.F., "Human gene therapy," *Nature,* 392(Suppl 6679):25–30 (1998).

(List continued on next page.)

*Primary Examiner*—Karen A. Lacourciere
(74) *Attorney, Agent, or Firm*—Hamilton, Brook, Smith & Reynolds, P.C.

(57) ABSTRACT

A versatile modular peptide mediated intracellular delivery system is disclosed which may be particularly adapted to facilitate the delivery of therapeutic compounds which are large in size or complex in nature. The invention relates both to a modular peptide mediated intracellular delivery system and a method of delivering a compound into a cell using the system.

17 Claims, 4 Drawing Sheets

OTHER PUBLICATIONS

Aramburu, J., et al., "Affinity–driven peptide selection of an NFAT inhibitor more selective than cyclosporin A," *Science*, 285:2129–2133 (1999).

Avrameas, A., et al., "Efficient gene delivery by a peptide derived from a monoclonal anti–DNA antibody," *Bioconjug. Chem.* 10:87–93 (1999).

Avrameas, A., et al., "Polyreactive anti–DNA monoclonal antibodies and a derived peptide as vectors for the intracytoplasmic and intranuclear translocation of macromolecules," *Proc. Natl. Acad. Sci. USA*, 95:5601–5606 (1998).

Bab, I., et al., "Biosynthesis of Osteogenic Growth Peptide via Alternative Translational Initiation at $AUG_{85}$ of Histone H4 mRNA," *The Journal of Biological Chemistry*, 274(20):14474–14481 (1999).

Barbier, B., and Brack, A., "Conformation–Controlled Hydrolysis of Polyribonucleotides by Sequential Basic Polypeptides," *J. Am. Chem. Soc.*, 114:3511–3515 (1992).

Baxevanis, A., and Landsman, D., "Histone Sequence Database: new histone fold family members," *Nucleic Acids Research*, 26(1):372–375 (1998).

Beasley, J., and Hecht, M., "Protein Design: The Choice of de Nova Sequences," *The Journal of Biological Chemistry*, 272(4):2031–2034 (1997).

Bralet, M.P., et al., "Cell Lineage Study in the Liver Using Retroviral Mediated Gene Transfer," *American Journal of Pathology*, 144(5):896–904 (1994).

Chakrabartty, A., et al., "Helix capping propensities in peptides parallel those in proteins," *Proc. Natl. Acad. Sci. USA*, 90:11332–11336 (1993).

Chalfie, M., et al., "Green Fluorescent Protein as a Marker for Gene Expression," *Science*, 263:802–805 (1994).

Chatelin, L., et al., "Transcription factor Hoxa–5 is taken up by cells in culture and conveyed to their nuclei," *Mechanisms of Development*, 55:111–117 (1996).

Chen, J., et al., "A novel gene delivery system using EGF receptor–mediated endocytosis," *FEBS Letters*, 338:167–169 (1994).

Cotten, M., et al., "High–efficiency receptor–mediated delivery of small and large (48 kilobase gene constructs using the endosome–disruption activity of defective or chemically inactivated adenovirus particles," *Proc. Natl. Acad. Sci. USA*, 89:6094–6098 (1992).

Crystal, R. G., "Transfer of Genes to Humans: Early Lessons and Obstacles to Success," *Science*, 270:404–410 (1995).

Damante, G., et al., "A molecular code dictates sequence–specific DNA recognition by homeodomains," *The EMBO Journal*, 15(18):4992–5000 (1996).

Darquet, A–M., et al., "Minicircle: an improved DNA molecule for in vitro and in vivo gene transfer," *Gene Therapy*, 6:209–218 (1999).

de Nooy, A. E. J., et al., "Highly selective nitroxyl radical–mediated oxidation of primary alcohol groups in water–soluble glucans," *Carbohydrate Research*, 269:89–98 (1995).

Derer, W., et al., "Direct protein transfer to terminally differentiated muscle cells," *J. Mol. Med.* 77:609–613 (1999).

Derossi, D., et al., "Trojan peptides: The penetratin system for intracellular delivery," *Trends Cell Biol.* 8:84–87 (1998).

Derossi, D., et al., "The Third Helix of the Antennapedia Homeodomain Translocates through Biological Membranes," *The Journal of Biological Chemistry*, 269(14):10444–10450 (1994).

Derossi, D., et al., "Cell Internalization of the Third Helix of the Antennapedia Homeodomain Is Receptor–independent," *The Journal of Biological Chemistry*, 271(30):18188–18193 (1996).

Diebold, S.S., et al., "Efficient Gene Delivery into Human Dendritic Cells by Adenovirus Polyethylenimine and Mannose Polyethylenimine Transfection," *Human Gene Therapy*, 10:775–786 (1999).

DiGabriele, A.D., et al., "Structure of a heparin–linked biologically active dimer of fibroblast growth factor," *Nature*, 393:812–817 (1998).

Dilber, M.S., et al., "Intracellular delivery of thymidine kinase prodrug activating enzyme by the herpes simplex virus protein, VP22," *Gene Therapy*, 6:12–21 (1999).

Dorn, A., et al., "Homeodomain Proteins in Development and Therapy," *Pharmac. Ther.*, 61:155–183 (1994).

Douglas, J. T., and Curiel, D.T., "Adenoviruses as Vectors for Gene Therapy," *Science & Medicine*, pp. 44–53 (Mar./Apr. 1997).

Dove, A., and Marshall, A., "Proteins break on through to the other side," *Nature Biotechnology*, 17:942 (1999).

Duguid, J.G., et al., "A Physicochemical Approach for Predicting the Effectiveness of Peptide–Based Gene Delivery Systems for Use in Plasmid–Based Gene Therapy," *Biophysical Journal*, 74:2802–2814 (1998).

Durell, S. R., et al., "What studies of fusion peptides tell us about viral envelope glycoprotein–mediated membrane fusion (Review)," *Molecular Membrane Biology*, 14:97–112 (1997).

Efthymiadis, A., et al., "The HIV–1 Tat nuclear localization sequence confers novel nuclear import properties," *J. Biol. Chem.*, 273:1623–1628 (1998).

Elliot, G. and O'Hare, P.,"Intercellular trafficking and protein delivery by a herpesvirus structural protein," *Cell*, 88:223–233 (1997).

Elliot, G. and O'Hare, P., "Intercellular trafficking of VP22–GFP fusion proteins," *Gene Therapy*, 6:149–151 (1999).

Ennist, D.L., "Gene therapy for lung disease," *Trends Pharmacol. Sci.* 20:260–266 (1999).

Erbacher, P., et al., "Gene transfer with synthetic virus–like particles via the integrin–mediated endocytosis pathway," *Gene Therapy*, 6:138–145 (1999).

Fawell, S., et al., "Tat–mediated delivery of heterologous proteins into cells," *Proc. Natl. Acad. Sci. USA*, 91:664–648 (1994).

Fasbender, A., et al., "Complexes of Adenovirus with Polycationic Polymers and Cationic Lipids Increase the Efficiency of Gene Transfer in Vitro and In Viro," *The Journal of Biological Chemistry*, 272(10):6479–6489 (1997).

Ferrari, S., et al., "Polyethylenimine shows properties of interest for cystic fibrosis gene therapy," *Biochim. Biophys. Acta*, 1447:219–225 (1999).

Ferry, N., and Heard, J.M., "Liver–Directed Gene Transfer Vectors," *Human Gene Therapy*, 9:1975–1981 (1998).

Feyzi, E., et al., "Characterization of Heparin and Heparan Sulfate Domains Binding to the Long Splice Variant of Platelet–derived Growth Factor A Chain," *The Journal of Biological Chemistry*, 272 (9):5518–5524 (1997).

Friedmann, T., "The Road toward Human Gene Therapy—A 25–year Perspective," *Annals of Medicine*, 29:575–577 (1997).

Gorecki, D. C. and MacDermot, K.D., "Gene therapy: Panacea or placebo? II. Main applications of gene therapy," *Arch. Immunol. Ther. Exp.*, 45:375–381 (1997).

Hammer, J., et al., "Precise Prediction of Major Histocompatibility Complex Class II–Peptide Interaction Based on Peptide Side Chain Scanning," *J. Exp. Med.*, 180:2353–2358 (1994).

Harbottle, R.P., et al., "An RGD–Oligolysine Peptide: A Prototype Construct for Integrin–Mediated Gene Delivery," *Human Gene Therapy*, 9:1037–1047 (1998).

Harrison, S.C., "A structural taxonomy of DNA–binding domains," *Nature*, 353:715–719 (1991).

Hashida, M., et al., "Targeted delivery of plasmid DNA complexed with galactosylated poly(L–lynsine)," *Journal of Controlled Release*, 53:301–310 (1998).

Hernandez, L.D., et al., "Virus–Cell and Cell–Cell Fusion," *Annu. Rev. Cell Dev. Biol.*, 12:627–661 (1996).

Hershfield, M.D., "Adenosine deaminiase deficiency: Clinical expression, molecular basis, and therapy," *Semin. Hematol.*, 35:291–298 (1998).

Hodgson, C.P., and Solaiman, F.A., "Future Vector Systems." In *Retro–Vectors for Human Gene Therapy*, R.G. Landes Company, eds., (Chapman & Hall), pp. 129–145 (1996).

Hogonson, D., et al., "Targeted Delivery of DNA Encoding Cytotoxic Proteins through High–Affinity Fibroblast Growth Factor Receptors," *Human Gene Therapy*, 9: 2565–2575 (1998).

Hoogerbrugge, P.M., et al., "Gene therapy for adenosine deaminase deficiency," *Br. Med. Bull.*, 51:72–81 (1995).

Hoogerbrugge, P.M., et al., "Bone marrow gene transfer in three patients with adenosine deaminase deficiency," *Gene Therapy*, 3:179–183 (1996).

Kang, S., et al., "Structural Requirements for Major Histocompatibility Complex Class II Invariant Chain Endocytosis and Lysosomal Targeting," *The Journal of Biological Chemistry*, 272(32):20644–20652 (1998).

Karn, J., "Tackling Tat," *J. Mol. Biol.*, 293:235–254 (1999).

Kasahara, N., et al., "Tissue–Specific Targeting of Retroviral Vectors Through Ligand–Receptor Interactions," *Science*, 266:1373–1376 (1994).

Kelleher, Z.T., et al., "Epstein–Barr–based episomal chromosomes shuttle 100 kb of self–replicating circular human DNA in mouse cells," *Nature Biotechnology*, 16:762–768 (1998).

Kichler, A., et al., "Influence of Membrane–Active Peptides on Lipospermine/DNA Complex Mediated Gene Transfer," *Bioconjugate Chem.*, 8:213–221 (1997).

Knight, A., et al., "Non–viral neuronal gene delivery mediated by the HC fragment of tetanus toxin," *Eur. J. Biochem.*, 259:762–769 (1999).

Koelle, D.M., et al., "Recognition of herpes simplex virus type 2 tegument proteins by CD4 T–cells infiltrating human genital herpes lesions," *J. Virol.*, 72:7476–7483 (1998).

Langreth, R., "Gene–Therapy Advance Is Made By Ariad and University Team," *The Wall Street Journal*, (Jan. 4, 1999).

Larocco, D., et al., "Gene transfer to mammalian cells using genetically targeted filamentous bacteriophage," *The FASEB Journal*, 13:727–734(1999).

LeRoux, I., et al., "Neurotrophic activity of the Antennapedia homeodomain depends on its specific DNA–binding properties," *Proc. Natl. Acad. Sci. USA*, 90:9120–9124 (1993).

Levine, A.J., "p53, the cellular gatekeeper for growth and division," *Cell*, 88:323–331 (1997).

Levine, A.J., "The tumor suppresser genes," *Annu. Rev. Biochem.* 62:623–651 (1993).

Lewis, B.S., et al., "Angiogenesis by gene therapy: A new horizon for myocardial revascularization?" *Cardiovasc. Res.*, 35:490–497 (1997).

Liu, F., et al., "Hydrodynamics–based transfection in animals by systemic administration of plasmid DNA," *Gene Therapy*, 6:1258–1266 (1999).

Ludtke, J.J., et al., "A nuclear localization signal can enhance both the nuclear transport and expression of 1 kb DNA," *Journal of Cell Science*, 112:2033–2041 (1999).

Luft, F.C., "Can VP22 resurrect gene therapy?" *J. Mol. Med.*, 77:575–576 (1999).

Mahato, R.I., et al., "Pharmaceutical perspectives of non–viral gene therapy," *Adv. Genet.*, 41:95–156 (1999).

Malashkevich, V.N.,et al., "Core structure of the envelope glycoprotein GP2 from Ebola virus at 1.9–Å resolution," *Proc. Natl. Acad. Sci. USA*, 96:2662–2667 (1999).

Mann, M.J., et al., "Pressure–mediated Oligonucleotide transfection of rat and human cardiovascular tissues," *Proc. Natl. Acad. Sci. USA*, 96:6411–6416 (1999).

Marshall, E., "Gene Therapy's Growing Pains," *Science*, 269:1050–1055 (1995).

McBrearty, B.A., et al., "Genetic analysis of a mammalian wound–healing trait," *Proc. Natl. Acad. Sci. USA*, 95:11792–11797 (1998).

Miao, H., et al., "Modulation of Fibroblast Growth Factor–2 Receptor Binding, Dimerization, Signaling, and Angiogenic Activity by a Synthetic Heparin–mimicking Polyanionic Compound," *J. Clin. Invest.*, 99(7):1565–1575 (1997).

Morris, M.C., et al., "A novel potent strategy for gene delivery using a single peptide vector as a carrier," *Nucl. Acid Res.*, 27:3510–3517 (1999).

Morris, M.C., et al., "A new peptide vector for efficient delivery of oligonucleotides into mammalian cells," *Nucl. Acid Res.*, 25:2730–2736 (1997).

Müller, M., et al., "Isolation and sequence–specific DNA binding of the Antennapedia homeodomain," *The EMBO Journal*, 7(13):4299–4304 (1988).

Mulligan, R.C., "The Basic Science of Gene Therapy," *Science*, 260:926–932 (1993).

Nielsen, M.S., et al., "Segments in the C–terminal Folding Domain of Lipoprotein Lipase Important for Binding to the Low Density Lipoprotein Receptor–related Protein and to Heparan Sulfate Proteoglycans," *The Journal of Biological Chemistry*, 272(9):5821–5827 (1997).

Niidome, T., et al., "Chain length of cationic α–helical peptide sufficient for gene delivery into cells," *Bioconjug. Chem.*, 10:773–780 (1999).

Norman, T.C., et al., "Genetic selection of peptide inhibitors of biological pathways," *Science*, 285:591–595 (1999).

Pack, D.W., et al., "Design of imidazole–containing endosomolytic biopolymers for gene delivery," *Biotechnol. Bioeng.*, 67:217–223 (2000).

Paillard, F., "Oligoplexes: Nonviral Vehicles for Receptor–Mediated Delivery," *Human Gene Therapy*, 9:987–988 (1998).

Pasqualini R. and Ruoslahti, E., "Organ targeting in vivo using phage display peptide libraries," *Nature*, 380:364–366 (1996).

Perez, F., et al., "Antennapedia homeobox as a signal for the cellular internalization and nuclear addressing of a small exogenous peptide," *Journal of Cell Science, 102:717–722* (1992).

Petrovas, C.J., et al., "A major Sm epitope anchored to sequential oligopeptide carriers is a suitable antigenic substrate to detect anti-Sm antibodies," *Journal of Immunological Methods, 220:59–68* (1998).

Phelan, A., et al., "Intracellular delivery of functional p53 by the herpesvirus protein VP22," *Nature Biotechnol.,* 16:440–443 (1998).

Plank, C., et al., "Branched Cationic Peptides for Gene Delivery: Role of Type and Number of Cationic Residues in Formation and in Vitro Activity of DNA Polyplexes," *Human Gene Therapy, 10:319–332* (1999).

Plank, C., et al., "The Influence of Endosome–disruptive Peptides on Gene Transfer Using Synthetic Virus–like Gene Transfer Systems," *The Journal of Biological Chemistry, 269(17):12918–12924* (1994).

Pooga, M., et al., "Cell penetrating PNA constructs regulate galanin receptor levels and modify pain transmission in vivo," *Nature Biotechnol.*, 16:857–861 (1998).

Qian, Y. Q., et al., "The des(1–6) Antennapedia homeodomain: Comparison of the NMR solution structure and the DNA–binding affinity with the intact Antennapedia homeodomain," *Proc. Natl. Acad. Sci USA, 91:4091–4095* (1994).

Roberts, R.W. and Szostak, J.W., "RNA–peptide fusions for the in vitro selection of peptides and proteins," *Proc. Natl. Acad. Sci. USA*, 94:12297–12302 (1997).

Roberts, R.W., "Totally in vitro protein selection using mRNA–protein fusions and ribosome display," *Curr. Opin. Chem. Biol.*, 3:268–273 (1999).

Romanczuk, H., et al., "Modification of an adenoviral vector with biologically selected peptides: A novel strategy for gene delivery to cells of choice," *Hum. Gene Ther.,* 10:2615–2626 (1999).

Sakarellos, C., et al., "Sequential Oligopeptide Carriers $(SOC_n)$ for Producing Potent Antigens and Effective Immunogens," In *Cytotoxic, Mutagenic and Carcinogenic Potential of Heavy Metals Related to Human Enviroment*, N. D. Hadjiliadis, ed., (Netherlands:Kluwer Academic Publishers), pp. 605–614 (1997).

Sakarellos, C., et al., "A New, Helicoid–Type, Oligopeptide Carrier for Therapeutic Applications in Autoimmune Diseases," In *Peptides*, S. Bajusz, et al., eds. (Budapest:Akademiai Kiado), pp. 76–77 (1998).

Sakarellos, C., et al., "A Conformationally Based Rational Design of Multiple Antigenic Peptide Carriers: The Potential for Disease Treatment," In *Peptides: Chemistry, Structure and Biology*, Kaumaya, P. T. P., et al., eds. (England:Mayflower Scientific Ltd.), pp. 816–817 (1996).

Sakarellos, C., et al., "The PPGMRPP repetitive epitope of the Sm autoantigen: Antigenic specificity induced by conformational changes. Application of the Sequential Oligopeptide Carriers (SOCs)," *Letters in Peptide Science, 4:447–454* (1997).

Sakarellos–Daitsiotis, M., et al., "A new helicoid–type sequential oligopeptide carrier $(SOC_n)$ for developing potent antigens and immunogens," *Vaccine, 00:1–9* (1999).

Sakarellos–Daitsiotis, M., et al., "Peptide Carriers: A New Helicoid–Type Sequential Oligopeptide Carrier $(SOC_n)$ for Multiple Anchoring of Antigenic/Immunogenic Peptides." In *Methods*, D. Boraschi, et al., eds., (Academic Press), pp. 1–28 (1999).

Sakarellos–Daitsiotis, M., et al., "Carriers of Peptide Epitopes for the Development of Specific Diagnostic Immunoassays and Protective Immunity," *Hellenic Forum on Bioactive Peptides*, pp. 311–326 (1997).

Schaffer, D.V.,et al., "Use of the Green Fluorescent Protein as a Quantitative Reporter of Epidermal Growth Factor Receptor–Mediated Gene Delivery," *Tissue Engineering, 3(1):53–63* (1997).

Schaffer, D.V., and Lauffenburger, D.A., "Optimization of Cell Surface Binding Enhances Efficiency and Specificity of Molecular Conjugate Gene Delivery," *The Journal of Biological Chemistry, 272(43):28004–28009* (1998).

Schindelhauer, D., "Construction of mammalian artificial chromosome: prospects for defining an optimal centromere," *BioEssays, 21:76–83* (1999).

Schneider, H., et al., "Targeted gene delivery into α9β1–integrin–displaying cells by a synthetic peptide," FEBS Lett 458:329–332 (1999).

Schwartz, B., et al., "Synthetic DNA–compacting peptides derived from human sequence enhance cationic lipid–mediated gene transfer in vitro and in vivo," *Gene Therapy, 6:282–292* (1999).

Schwarze, S.R., et al., "In Vivo Protein Transduction: Delivery of a Biologically Active Protein into the Mouse," *Science, 285:1569–1572* (1999).

Shewring, L., et al., "A non–viral vector system for efficient gene transfer to corneal endothelial cells via membrane integrins," *Transplantation*, 64:763–769 (1997).

Shimizu, N., et al., "Immunogene approach toward cancer therapy using erythrocyte growth factor receptor–mediated gene delivery," *Cancer Gene Therapy, 3(2):113–120* (1996).

Singh, M., et al., "LearnCoil–VMF: Computational Evidence for Coiled–coil–like Motifs in Many Viral Membrane– fusion Proteins," *J. Mol. Biol., 290:1031–1041* (1999).

Singh, D., et al., "Peptide–based intracellular shuttle able to facilitate gene transfer in mammalian cells," *Bioconjug Chem* 10:745–754 (1999).

Spillmann, D., et al., "Defining the Interleukin–8–binding Domain of Heparan Sulfate," *The Journal of Biological Chemistry, 273(25):15487–15493* (1998).

Taraboletti, G., et al., "Thrombospondin–1 inhibits Kaposi's sarcoma (KS) cell and HIV–1 Tat–induced angiogenesis and is poorly expressed in KS lesions," J. Pathol., 188:76–81 (1999).

Trybala, E., et al., "Interaction between Pseudorabies Virus and Heparin/Heparan Sulfate," *The Journal of Biological Chemistry, 273(9):5047–5052* (1998).

Tsikaris, V., et al., "Use of Sequential Oligopeptide Carriers $(SOC_n)$ in the Design of Potent Leishmania gp63 Immunogenic Peptides," *Peptide Research, 9(5):240–247* (1996).

Tsikaris, V., et al., "Concept and Design of a New Class of Sequential Oligopeptide Carriers (SOC) for Covalent Attachment of Multiple Antigenic Peptides," *Biopolymers, 38:291–293* (1996).

Tsikaris, V., et al., "Immunoreactivity and conformation of the P–P–G–M–R–P–P repetitive epitope of the Sm autoantigen," *Int. J. Peptide Protein Res., 48:319–327* (1996).

Tsikaris, V., et al., "Construction and application of a new class of sequential oligopeptide carriers (SOC$_n$) for multiple anchoring of antienic peptides–application to the acetylcholine receptor (AChR)main immunogenic region," *International Journal of Biological Macromolecules, 19:195–205* (1996).

van Kuppevelt, T.H., et al., "Generation and Application of Type–specific Anti–Heparan Sulfate Antibodies Using Phage Display Technology," *The Journal of Biological Chemistry, 273(21):12960–12966* (1998).

Vassalli, G. and Dichek, D.A., "Gene therapy for arterial thrombosis," *Cardiovasc Res.*, 35:459–469 (1997).

Verderio, C., et al., "Calcium–dependent glutamate release during neuronal development and synaptogenesis: Different involvement of ώ–agatoxin IVA–and ώ–conotoxin GVI-A–sensitive channels," *Proc. Natl. Acad.Sci. USA, 92:6449–6453* (1995).

Verma, I.M., and Somia, N., "Gene therapy–promises, problems and prospects," *Nature, 389:239–242* (1997).

Vives, E., et al., "A Truncated HIV–1 Tat Protein Basic Domain Rapidly Translocates through the Plasma Membrane and Accumulates in the Cell Nucleus," *The Journal of Biological Chemistry, 272(25):16010–16017* (1997).

Wadhwa, M.S., et al., "Peptide–mediated gene delivery: Influence of peptide structure on gene expression," *Bioconjug. Chem.* 8:81–88 (1997).

Weis, K., "Importins and exportins: how to get in and out of the nucleus," *TIBS*, pp. 185–189 (May, 1998).

Williams, E.J., et al., "Selective inhibition of growth factor–stiumlated mitogenesis by a cell–permeable Grb2–binding peptide," *J. Biol Chem.*, 272:22349–22354 (1997).

Wong, P., et al., "Analysis of Putative Heparin–binding Domains of Fibroblast Growth Factor–1," *The Journal of Biological Chemistry, 270(43):25805–25811* (1995).

Wu,G. Y., and Wu, C.H., "Receptor–mediated in Vitro Gene Transformation by a Soluble DNA Carrier System," *The Journal of Biological Chemistry, 262(10):4429–4432* (1987).

Wu, G.Y., and Wu, C. H., "Receptor–mediated Gene Delivery and Expression in Vivo," *The Journal of Biological Chemistry, 263(29):14621–14624* (1988).

Ye, X., et al., "Regulated Delivery of Therapeutic Proteins After in Vivo Somatic Cell Gene Transfer," *Science, 283:88–91* (1999).

Yiannaki, E.E., et al., "The value of synthetic linear epitope analogues of La/SSB for the detection of autoantibodies to La/SSB; specificity, sensitivity and comparison of methods," *Clinical and Experimental Immunology, 112:152–158* (1998).

Yla–Herttuala, S., "Vascular gene transfer," Curr. Opin. Lipidol., 8:72–76 (1997).

Zanta, M.A., et al., "Gene delivery: A single nuclear localization signal peptide is sufficient to carry DNA to the cell nucleus," *Proc Natl Acad Sci USA*, 96:91–96 (1999).

Zauner, W., et al., "Gycerol and Polylysine Synergize in Their Ability to Rupture Vesicular Membranes: A Mechanism for Increased Transferrin–Polylysine–Mediated Gene Transfer," *Experimental Cell Research, 232:137–145* (1997).

Ziady, A.G., et al., "Ligand substitution of receptor targeted DNA complexes affects gene transfer into hepatoma cells," *Gene Therapy*, 5:1685–1697 (1998).

Zurawski, S.M., and Zurawski, G., "Mouse interleukin–2 structure–function studies: substitutions in the first α–helix can specifically inactivate p70 receptor binding and mutations in the fifth α–helix can specifically inactivate p55 receptor binding," *The EMBO Journal, 8(9):2583–2590* (1989).

\* cited by examiner

Receptor Recognition Ligand — N-[...]G-G[Membrane Fusion]G-G[Binding Peptide]-C

FIG. 1A

Membrane Fusion — N-[...]G-G[Receptor Recognition Ligand]G-G[Binding Peptide]-C

Homogeneous Branched Peptide

Heterogeneous Branched Peptide
A) General Delivery

B) Specific Delivery

- Lysine-rich Backbone
- Membrane Fusion Component
- Binding Peptide Nuclear Localization Component
- Receptor Recognition Ligand Component
- EpiTag

SEQUENCE LISTING

```
<160> NUMBER OF SEQ ID NOS: 45

<210> SEQ ID NO 1
<211> LENGTH: 45
<212> TYPE: PRT
<213> ORGANISM: Artificial Sequence
<220> FEATURE:
<223> OTHER INFORMATION: synthetic

<400> SEQUENCE: 1

Asn Tyr Arg Asn Leu Lys Leu Pro Arg Met Leu Thr Phe Lys Phe Tyr
1               5                   10                  15

Leu Gly Gly Trp Ala Glu Ser Leu Gly Glu Ala Leu Glu Gly Gly Lys
            20                  25                  30

Lys Ser Ile Lys Lys Thr Ala Lys Lys Val Lys Lys Lys
        35                  40                  45

<210> SEQ ID NO 2
<211> LENGTH: 45
<212> TYPE: PRT
<213> ORGANISM: Artificial Sequence
<220> FEATURE:
<223> OTHER INFORMATION: synthetic
```

```
<400> SEQUENCE: 2

Asn Tyr Arg Asn Leu Lys Leu Pro Arg Met Leu Thr Phe Lys Phe Tyr
 1               5                  10                 15

Leu Gly Gly Ala Ile Gly Leu Ala Trp Ile Pro Tyr Phe Gly Pro Ala
            20                  25                  30

Ala Glu Gly Gly Lys Lys Lys Arg Lys Val Lys Lys
        35                  40                  45

<210> SEQ ID NO 3
<211> LENGTH: 45
<212> TYPE: PRT
<213> ORGANISM: Artificial Sequence
<220> FEATURE:
<223> OTHER INFORMATION: synthetic

<400> SEQUENCE: 3

Leu Glu Asp Glu Leu Gly Pro Leu Arg His Val Leu Asp Leu Thr Gln
 1               5                  10                 15

Ser Gly Gly Trp Ala Glu Ser Leu Gly Glu Ala Leu Glu Gly Gly Lys
            20                  25                  30

Lys Ser Ile Lys Lys Thr Ala Lys Lys Val Lys Lys Lys
        35                  40                  45

<210> SEQ ID NO 4
<211> LENGTH: 46
<212> TYPE: PRT
<213> ORGANISM: Artificial Sequence
<220> FEATURE:
<223> OTHER INFORMATION: synthetic

<400> SEQUENCE: 4

Leu Glu Asp Glu Leu Gly Pro Leu Arg His Val Leu Asp Leu Thr Gln
 1               5                  10                 15

Ser Gly Gly Ala Ile Gly Leu Ala Trp Ile Pro Tyr Phe Gly Pro Ala
            20                  25                  30

Ala Glu Gly Gly Lys Lys Ser Lys Lys Thr Lys Lys Val Lys
        35                  40                  45

<210> SEQ ID NO 5
<211> LENGTH: 45
<212> TYPE: PRT
<213> ORGANISM: Artificial Sequence
<220> FEATURE:
<223> OTHER INFORMATION: synthetic

<400> SEQUENCE: 5

Trp Ala Glu Ser Leu Gly Glu Ala Leu Glu Gly Gly Asn Tyr Arg Asn
 1               5                  10                 15

Leu Lys Leu Pro Arg Met Leu Thr Phe Lys Phe Tyr Leu Gly Gly Lys
            20                  25                  30

Lys Ser Ile Lys Lys Thr Ala Lys Lys Val Lys Lys Lys
        35                  40                  45

<210> SEQ ID NO 6
<211> LENGTH: 45
<212> TYPE: PRT
<213> ORGANISM: Artificial Sequence
<220> FEATURE:
<223> OTHER INFORMATION: synthetic

<400> SEQUENCE: 6
```

```
Trp Ala Glu Ser Leu Gly Glu Ala Leu Glu Gly Gly Leu Glu Asp Glu
 1               5                  10                  15

Leu Gly Pro Leu Arg His Val Leu Asp Leu Thr Gln Ser Gly Gly Lys
            20                  25                  30

Lys Ser Ile Lys Lys Thr Ala Lys Val Lys Lys
            35                  40              45
```

<210> SEQ ID NO 7
<211> LENGTH: 46
<212> TYPE: PRT
<213> ORGANISM: Artificial Sequence
<220> FEATURE:
<223> OTHER INFORMATION: synthetic

<400> SEQUENCE: 7

```
Ala Ala Ile Gly Leu Ala Trp Ile Pro Tyr Phe Gly Pro Ala Ala Glu
 1               5                  10                  15

Gly Gly Asn Tyr Arg Asn Leu Lys Leu Pro Arg Met Leu Thr Phe Lys
            20                  25                  30

Phe Tyr Leu Gly Gly Lys Lys Lys Arg Lys Val Lys Lys
            35                  40              45
```

<210> SEQ ID NO 8
<211> LENGTH: 46
<212> TYPE: PRT
<213> ORGANISM: Artificial Sequence
<220> FEATURE:
<223> OTHER INFORMATION: synthetic

<400> SEQUENCE: 8

```
Ala Ile Gly Leu Ala Trp Ile Pro Tyr Phe Gly Pro Ala Ala Glu Gly
 1               5                  10                  15

Gly Leu Glu Asp Glu Leu Gly Pro Leu Arg His Val Leu Asp Leu Thr
            20                  25                  30

Gln Ser Gly Gly Lys Lys Ser Lys Thr Lys Lys Lys
            35                  40              45
```

<210> SEQ ID NO 9
<211> LENGTH: 26
<212> TYPE: PRT
<213> ORGANISM: Artificial Sequence
<220> FEATURE:
<223> OTHER INFORMATION: synthetic

<400> SEQUENCE: 9

```
Trp Ala Glu Ser Leu Gly Glu Ala Leu Glu Gly Gly Lys Lys Ser Ile
 1               5                  10                  15

Lys Lys Thr Ala Lys Lys Val Lys Lys
            20                  25
```

<210> SEQ ID NO 10
<211> LENGTH: 27
<212> TYPE: PRT
<213> ORGANISM: Artificial Sequence
<220> FEATURE:
<223> OTHER INFORMATION: synthetic

<400> SEQUENCE: 10

```
Ala Ile Gly Leu Ala Trp Ile Pro Tyr Phe Gly Pro Ala Ala Glu Gly
 1               5                  10                  15

Gly Lys Lys Ser Lys Lys Thr Lys Val Lys
            20                  25
```

<210> SEQ ID NO 11
<211> LENGTH: 29
<212> TYPE: PRT
<213> ORGANISM: Artificial Sequence
<220> FEATURE:
<223> OTHER INFORMATION: synthetic

<400> SEQUENCE: 11

Leu Glu Asp Glu Leu Gly Pro Leu Arg His Val Leu Asp Leu Thr Gln
 1               5                  10                  15

Ser Gly Gly Trp Ala Glu Ser Leu Gly Glu Ala Leu Glu
            20                  25

<210> SEQ ID NO 12
<211> LENGTH: 35
<212> TYPE: PRT
<213> ORGANISM: Artificial Sequence
<220> FEATURE:
<223> OTHER INFORMATION: synthetic

<400> SEQUENCE: 12

Asn Tyr Arg Asn Leu Lys Leu Pro Arg Met Leu Thr Phe Lys Phe Tyr
 1               5                  10                  15

Leu Gly Gly Ala Ala Ile Gly Leu Ala Trp Ile Pro Tyr Phe Gly Pro
            20                  25                  30

Ala Ala Glu
        35

<210> SEQ ID NO 13
<211> LENGTH: 25
<212> TYPE: PRT
<213> ORGANISM: Artificial Sequence
<220> FEATURE:
<223> OTHER INFORMATION: synthetic

<400> SEQUENCE: 13

Arg Pro Lys Ala Lys Ala Lys Ala Lys Asp Gln Thr Lys Lys
 1               5                  10                  15

Lys Lys Lys Arg Lys Val Lys Lys Ala
            20                  25

<210> SEQ ID NO 14
<211> LENGTH: 26
<212> TYPE: PRT
<213> ORGANISM: Artificial Sequence
<220> FEATURE:
<223> OTHER INFORMATION: synthetic

<400> SEQUENCE: 14

Trp Ala Glu Ser Leu Gly Glu Ala Leu Glu Gly Lys Lys Ser Ile
 1               5                  10                  15

Lys Lys Thr Ala Lys Lys Val Lys Lys Lys
            20                  25

<210> SEQ ID NO 15
<211> LENGTH: 27
<212> TYPE: PRT
<213> ORGANISM: Artificial Sequence
<220> FEATURE:
<223> OTHER INFORMATION: synthetic

<400> SEQUENCE: 15

Ala Ile Gly Leu Ala Trp Ile Pro Tyr Phe Gly Pro Ala Ala Glu Gly
 1               5                  10                  15

```
Gly Lys Lys Ser Lys Lys Thr Lys Lys Val Lys
            20              25
```

<210> SEQ ID NO 16
<211> LENGTH: 18
<212> TYPE: PRT
<213> ORGANISM: Artificial Sequence
<220> FEATURE:
<223> OTHER INFORMATION: synthetic

<400> SEQUENCE: 16

```
Leu Gly Ile Ser Tyr Gly Arg Lys Lys Arg Arg Gln Arg Arg Arg Pro
 1               5                  10                  15

Pro Gln
```

<210> SEQ ID NO 17
<211> LENGTH: 11
<212> TYPE: PRT
<213> ORGANISM: Artificial Sequence
<220> FEATURE:
<223> OTHER INFORMATION: synthetic

<400> SEQUENCE: 17

```
Pro Lys Lys Lys Arg Lys Val Glu Asp Pro Tyr
 1               5                  10
```

<210> SEQ ID NO 18
<211> LENGTH: 11
<212> TYPE: PRT
<213> ORGANISM: Artificial Sequence
<220> FEATURE:
<223> OTHER INFORMATION: synthetic

<400> SEQUENCE: 18

```
Trp Ala Lys Ser Leu Gly Lys Ala Leu Lys Cys
 1               5                  10
```

<210> SEQ ID NO 19
<211> LENGTH: 16
<212> TYPE: PRT
<213> ORGANISM: Artificial Sequence
<220> FEATURE:
<223> OTHER INFORMATION: synthetic

<400> SEQUENCE: 19

```
Ala Ala Ile Gly Leu Ala Trp Ile Pro Tyr Phe Gly Pro Ala Ala Glu
 1               5                  10                  15
```

<210> SEQ ID NO 20
<211> LENGTH: 23
<212> TYPE: PRT
<213> ORGANISM: Artificial Sequence
<220> FEATURE:
<223> OTHER INFORMATION: synthetic

<400> SEQUENCE: 20

```
Glu Lys Met Ser Thr Ala Ile Ser Val Leu Leu Ala Gln Ala Val Phe
 1               5                  10                  15

Leu Leu Leu Thr Ser Gln Arg
            20
```

<210> SEQ ID NO 21
<211> LENGTH: 18
<212> TYPE: PRT
<213> ORGANISM: Artificial Sequence

```
<220> FEATURE:
<223> OTHER INFORMATION: synthetic

<400> SEQUENCE: 21

Leu Gly Leu Leu Leu Arg His Leu Arg His His Ser Asn Leu Leu Ala
 1               5                  10                  15

Asn Ile

<210> SEQ ID NO 22
<211> LENGTH: 23
<212> TYPE: PRT
<213> ORGANISM: Artificial Sequence
<220> FEATURE:
<223> OTHER INFORMATION: synthetic

<400> SEQUENCE: 22

Lys Gly Glu Val Cys Arg Leu Ala Gln Asp Glu Ala Asp Val Thr Glu
 1               5                  10                  15

Tyr Cys Asn Gly Thr Ser Glu
            20

<210> SEQ ID NO 23
<211> LENGTH: 23
<212> TYPE: PRT
<213> ORGANISM: Artificial Sequence
<220> FEATURE:
<223> OTHER INFORMATION: synthetic

<400> SEQUENCE: 23

Arg Gly Arg Leu Cys Arg Lys Ser Lys Asp Gln Ala Asp Phe Pro Glu
 1               5                  10                  15

Phe Cys Asn Gly Glu Thr Glu
            20

<210> SEQ ID NO 24
<211> LENGTH: 36
<212> TYPE: PRT
<213> ORGANISM: Artificial Sequence
<220> FEATURE:
<223> OTHER INFORMATION: synthetic

<400> SEQUENCE: 24

Tyr Thr Ser Leu Ile His Ser Leu Ile Glu Glu Ser Asn Gln Asn Gln
 1               5                  10                  15

Gln Glu Lys Asn Glu Gln Glu Leu Leu Glu Asp Lys Trp Ala Ser Leu
                20                  25                  30

Trp Asn Trp Phe
        35

<210> SEQ ID NO 25
<211> LENGTH: 20
<212> TYPE: PRT
<213> ORGANISM: Artificial Sequence
<220> FEATURE:
<223> OTHER INFORMATION: synthetic

<400> SEQUENCE: 25

Lys Lys Lys Lys Lys Lys Lys Lys Lys Lys Lys Lys Lys Lys Lys Lys
 1               5                  10                  15

Lys Lys Lys Lys
            20

<210> SEQ ID NO 26
```

```
<211> LENGTH: 20
<212> TYPE: PRT
<213> ORGANISM: Artificial Sequence
<220> FEATURE:
<223> OTHER INFORMATION: synthetic

<400> SEQUENCE: 26

Lys Ala Lys Ala Lys Ala Lys Ala Lys Ala Lys Ala Lys Ala Lys Ala
 1               5                  10                  15

Lys Ala Lys Ala
            20

<210> SEQ ID NO 27
<211> LENGTH: 20
<212> TYPE: PRT
<213> ORGANISM: Artificial Sequence
<220> FEATURE:
<223> OTHER INFORMATION: synthetic

<400> SEQUENCE: 27

Lys Gly Lys Gly Lys Gly Lys Gly Lys Gly Lys Gly Lys Gly Lys Gly
 1               5                  10                  15

Lys Gly Lys Gly
            20

<210> SEQ ID NO 28
<211> LENGTH: 30
<212> TYPE: PRT
<213> ORGANISM: Artificial Sequence
<220> FEATURE:
<223> OTHER INFORMATION: synthetic

<400> SEQUENCE: 28

Lys Ala Ala Lys Ala Ala Lys Ala Ala Lys Ala Ala Lys Ala Ala Lys
 1               5                  10                  15

Ala Ala Lys Ala Ala Lys Ala Ala Lys Ala Ala Lys Ala Ala
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: synthetic

<400> SEQUENCE: 29

Lys Gly Gly Lys Gly Gly Lys Gly Gly Lys Gly Gly Lys Gly Gly Lys
 1               5                  10                  15

Gly Gly Lys Gly Gly Lys Gly Gly Lys Gly Gly Lys Gly Gly
            20                  25                  30

<210> SEQ ID NO 30
<211> LENGTH: 33
<212> TYPE: PRT
<213> ORGANISM: Artificial Sequence
<220> FEATURE:
<223> OTHER INFORMATION: synthetic

<400> SEQUENCE: 30

Lys Pro Gly Lys Pro Gly Lys Pro Gly Lys Pro Gly Lys Pro Gly Lys
 1               5                  10                  15

Pro Gly Lys Pro Gly Lys Pro Gly Lys Pro Gly Lys Pro Gly Lys Pro
            20                  25                  30

Gly
```

```
<210> SEQ ID NO 31
<211> LENGTH: 16
<212> TYPE: PRT
<213> ORGANISM: Artificial Sequence
<220> FEATURE:
<223> OTHER INFORMATION: synthetic

<400> SEQUENCE: 31

Arg Gln Ile Lys Ile Trp Phe Gln Asn Arg Arg Met Lys Trp Lys Lys
 1               5                  10                  15

<210> SEQ ID NO 32
<211> LENGTH: 16
<212> TYPE: PRT
<213> ORGANISM: Artificial Sequence
<220> FEATURE:
<223> OTHER INFORMATION: synthetic

<400> SEQUENCE: 32

Lys Lys Trp Lys Met Arg Arg Asn Gln Phe Trp Ile Lys Ile Gln Arg
 1               5                  10                  15

<210> SEQ ID NO 33
<211> LENGTH: 16
<212> TYPE: PRT
<213> ORGANISM: Artificial Sequence
<220> FEATURE:
<223> OTHER INFORMATION: synthetic

<400> SEQUENCE: 33

Arg Gln Ile Lys Ile Trp Phe Gln Asn Arg Arg Met Lys Trp Lys Lys
 1               5                  10                  15

<210> SEQ ID NO 34
<211> LENGTH: 16
<212> TYPE: PRT
<213> ORGANISM: Artificial Sequence
<220> FEATURE:
<223> OTHER INFORMATION: synthetic

<400> SEQUENCE: 34

Arg Gln Ile Lys Ile Trp Phe Pro Asn Arg Arg Met Lys Trp Lys Lys
 1               5                  10                  15

<210> SEQ ID NO 35
<211> LENGTH: 16
<212> TYPE: PRT
<213> ORGANISM: Artificial Sequence
<220> FEATURE:
<223> OTHER INFORMATION: synthetic

<400> SEQUENCE: 35

Arg Gln Pro Lys Ile Trp Phe Pro Asn Arg Arg Lys Pro Trp Lys Lys
 1               5                  10                  15

<210> SEQ ID NO 36
<211> LENGTH: 16
<212> TYPE: PRT
<213> ORGANISM: Artificial Sequence
<220> FEATURE:
<223> OTHER INFORMATION: synthetic

<400> SEQUENCE: 36

Arg Gln Ile Lys Ile Phe Phe Gln Asn Arg Arg Met Lys Phe Lys Lys
 1               5                  10                  15
```

```
<210> SEQ ID NO 37
<211> LENGTH: 16
<212> TYPE: PRT
<213> ORGANISM: Artificial Sequence
<220> FEATURE:
<223> OTHER INFORMATION: synthetic

<400> SEQUENCE: 37

Arg Gln Ile Lys Ile Trp Phe Gln Asn Met Arg Arg Lys Trp Lys Lys
 1               5                  10                  15

<210> SEQ ID NO 38
<211> LENGTH: 16
<212> TYPE: PRT
<213> ORGANISM: Artificial Sequence
<220> FEATURE:
<223> OTHER INFORMATION: synthetic

<400> SEQUENCE: 38

Arg Gln Ile Arg Ile Trp Phe Gln Asn Arg Arg Met Arg Trp Arg Arg
 1               5                  10                  15

<210> SEQ ID NO 39
<211> LENGTH: 16
<212> TYPE: PRT
<213> ORGANISM: Artificial Sequence
<220> FEATURE:
<223> OTHER INFORMATION: synthetic

<400> SEQUENCE: 39

Arg Arg Trp Arg Arg Trp Trp Arg Arg Trp Trp Arg Arg Trp Arg Arg
 1               5                  10                  15

<210> SEQ ID NO 40
<211> LENGTH: 13
<212> TYPE: PRT
<213> ORGANISM: Artificial Sequence
<220> FEATURE:
<223> OTHER INFORMATION: synthetic

<400> SEQUENCE: 40

Cys Gly Phe Glu Cys Val Arg Gln Cys Pro Glu Arg Cys
 1               5                  10

<210> SEQ ID NO 41
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: (1)...(21)
<223> OTHER INFORMATION: Xaa = Any Amino Acid

<400> SEQUENCE: 41

Cys Asn Arg Cys Gly Gly Xaa Lys Leu Ala Lys Leu Ala Lys Lys Leu
 1               5                  10                  15

Ala Lys Leu Ala Lys
            20

<210> SEQ ID NO 42
<211> LENGTH: 16
<212> TYPE: PRT
<213> ORGANISM: Artificial Sequence
<220> FEATURE:
<223> OTHER INFORMATION: synthetic
```

```
<400> SEQUENCE: 42

Met Ala Gly Pro His Pro Val Ile Val Ile Thr Gly Pro His Glu Glu
 1               5                  10                  15

<210> SEQ ID NO 43
<211> LENGTH: 7
<212> TYPE: PRT
<213> ORGANISM: Artificial Sequence
<220> FEATURE:
<223> OTHER INFORMATION: synthetic

<400> SEQUENCE: 43

Pro Lys Lys Lys Arg Lys Val
 1               5

<210> SEQ ID NO 44
<211> LENGTH: 13
<212> TYPE: PRT
<213> ORGANISM: Artificial Sequence
<220> FEATURE:
<223> OTHER INFORMATION: synthetic

<400> SEQUENCE: 44

Arg Gln Val Phe Gln Val Ala Tyr Ile Ile Ile Lys Ala
 1               5                  10

<210> SEQ ID NO 45
<211> LENGTH: 5
<212> TYPE: PRT
<213> ORGANISM: Artificial Sequence
<220> FEATURE:
<223> OTHER INFORMATION: synthetic

<400> SEQUENCE: 45

Tyr Ile Gly Ser Arg
 1               5
```

MODULAR PEPTIDE MEDIATED INTRACELLULAR DELIVERY SYSTEM AND USES THEREFORE

GOVERNMENT SUPPORT

The invention was supported, in whole or in part, by a grant 1R21 RR 14010-01NIH from the National Institutes of Health. The Government has certain rights in the invention.

BACKGROUND OF THE INVENTION

The lack of effective intracellular delivery systems for therapeutic compounds continues to hamper the progress of many types of biological study, and impedes the development of clinical applications of that research. Intracellular delivery of many molecules can be difficult but the delivery of extremely large or complex molecules, such as the DNA that comprises human genes, is particularly problematic. For example, gene delivery has been described as "[T]he Achilles heel of gene therapy". (Verma, I. M. et al. 1997, Nature 389:239–242, 239) While gene therapy is universally recognized as having tremendous clinical potential, it has yet to achieve completely successful clinical results. (Friedmann, T., 1997, Ann. Med. 6:575–577)

At present, the majority of gene therapy systems rely on viral vectors for gene delivery. Retroviral, adeno-associated and other viral strains have all been utilized as nucleic acid vectors, due to their ability to infect a large proportion of target cells in a manner which results in stable integration of the nucleic acid in the cell. However, such vectors lack the capacity to deliver large DNA molecules and, in addition, difficulties with sustained protein expression in cells subsequent to viral infection have been widely reported. (Hodgson, C. et al., 1996, Retro-Vectors for Human Gene Therapy, Chapter 6, pp. 129–145) Furthermore, there are ever increasing concerns regarding the ability to safely use viral vectors in the clinical setting. (Crystal, R., 1995, Science 170:404–410)

Such concerns have resulted in increased interest in nonviral alternatives for intracellular compound delivery. One major hurdle in developing systems of this type is the inability of certain molecules, such as small molecules, proteins, peptides, oligonucleotides, and genes, to efficiently traverse the lipid bilayer of the cell plasma membrane or that of endosomal vesicles. Certain types of transport systems have been developed to allow compounds to enter cells through receptor mediated endocytosis in an attempt to solve the difficulties of efficient cell entry. These systems contain conjugates formed of a polycation domain which binds the delivery compound, and a ligand domain which targets a receptor for compound delivery. (Harbottle, R. P. et al., 1998, Human Gene Therapy 9:1037–1047; Schaffer, D. V. et al., 1998, J Biol Chem 43:28004–28009) However, the effectiveness of these systems is severely impacted by the degradation to the compounds which occurs in the endosomes following cell entry. (Palliard, F., 1998, Human Gene Therapy 9:987–988)

Another alternative to viral vectors are various cationic lipids, liposomes, that allow genes to cross the cell membrane. In general, the efficiency of delivery and sustained expression provided by these vectors has been poor. (Verma, I., et a. 1997, Nature 389:239–242) Moreover, there have been reports of toxic side effects with some liposomes.

Other systems have recently emerged which attempt to target the lipid bilayer component of the cell directly, and thus avoid the difficulties associated with receptor mediated endocytosis. Such systems generally contain a moiety able to translocate across biological membranes attached to the "cargo" intended for delivery. One such system, containing the protein transduction domain from the human immunodeficiency virus (HIV) TAT protein, has been used to deliver a β-galactosidase protein to cells in an animal model. (Schwarze, S.R et al., 1999, Science 285:1569–1572) Another such system, containing a portion of the homeodomain protein from antennapedia (hereinafter "ANT"), has demonstrated delivery of several small proteins and oligonucleotides to cells in culture. It has been reported, however, that monomeric homeodomains "lose their translocation abilities when they bind to DNA". (Derossi, D. et al., 1998, Trends in Cell Biology 8:84–87) Thus, the range of compounds which these systems are currently able to deliver is limited in type and size.

Therefore, there exists a need for a versatile system capable of effectively delivering a wide range of therapeutic compounds intracellularly.

SUMMARY OF THE INVENTION

The present invention is based, at least in part, on the discovery of a system useful for the intracellular delivery of a wide range of compounds. The system is comprised of various individual functional components linked together. The modular nature of the system permits specific optimization of the various functional aspects necessary to effectively accomplish intracellular delivery of cargo compounds. The system is very versatile and may be particularly adapted to facilitate the delivery of therapeutic compounds which are large in size or complex in nature. The invention relates both to a modular peptide mediated intracellular delivery system and a method of delivering a compound into a cell using the system.

In one aspect, the intracellular delivery system of the invention comprises a binding peptide component and a membrane fusion component comprising the ANT binding domain motif or its functional equivalent. In a preferred embodiment, the intracellular delivery system further comprises a receptor recognition ligand component.

In a preferred embodiment, the components are covalently bonded.

In a preferred embodiment, the components are attached to a backbone peptide comprising a plurality of charged, ionizable or reactive amino acid molecules, e.g., lysine or aspartic acid. The peptide may be linear, branched or circular. In a particularly preferred embodiment, the amino acid molecule of the linear peptide is lysine.

In a preferred embodiment, the system is intended to or can deliver a nucleic acid, e.g., RNA or DNA. In a preferred embodiment, the system is intended to or can deliver DNA comprising a coding region under functional control of a promoter. In a particularly preferred embodiment, the system is intended to or can deliver DNA under functional control of its naturally-occurring regulatory elements.

In a preferred embodiment, the binding peptide component is a histone derived peptide.

In another aspect of the invention, the intracellular delivery system comprises a plurality of membrane fusion components comprising the ANT binding domain motif or its functional equivalent and a cargo component. In a preferred embodiment, the delivery system further comprises a binding peptide component. In a preferred embodiment, the delivery system further contains a receptor recognition ligand component. In a particularly preferred embodiment, the delivery system further comprises both a binding peptide component and a receptor recognition ligand component.

In a preferred embodiment, the components are covalently bonded.

In a preferred embodiment, the components are attached to a peptide, a "backbone", comprising a plurality of charged, ionizable or reactive amino acid molecules, e.g., lysine or aspartic acid. The backbone can be linear, branched or circular. In a preferred embodiment, the amino acid molecule of the peptide is lysine.

In a preferred embodiment, the membrane fusion component is bound to the backbone peptide at the available reactive center. The available reactive site for lysine is at the $\epsilon$-N side chain.

In a preferred embodiment, the system is intended to or can deliver a nucleic acid, e.g., RNA or DNA. In a preferred embodiment, the system is intended to or can deliver DNA containing a coding region under functional control of a promoter. In a particularly preferred embodiment, the system is intended to or can deliver DNA under functional control of its naturally-occurring regulatory elements.

In a preferred embodiment, the binding peptide component is a histone derived peptide.

In yet another aspect, the invention relates to a method of delivering selected cargo into a cell comprising the steps of attaching the selected cargo to an intracellular delivery system comprising a binding peptide component and a membrane fusion component composed of the ANT binding domain motif or its functional equivalent, under conditions suitable for formation of a cargo-delivery system complex; introducing the cargo-delivery system complex to the surface of the cell; and delivering the complex into the cell.

In a preferred embodiment, the cargo is a nucleic acid, e.g., RNA or DNA. In a preferred embodiment, the cargo is DNA containing a coding region under functional control of a promoter. In a particularly preferred embodiment, the cargo DNA is under functional control of its naturally-occurring regulatory elements.

In a preferred embodiment, the method further comprises a step of utilizing the transfected cell in gene therapy.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 1A–1B are illustrations of intracellular delivery systems of the invention containing a receptor recognition ligand component, a membrane fusion peptide component and a binding peptide component.

FIG. 3 is an illustration of an alternate intracellular delivery system of the invention.

DETAILED DESCRIPTION OF THE INVENTION

Figure 2A:
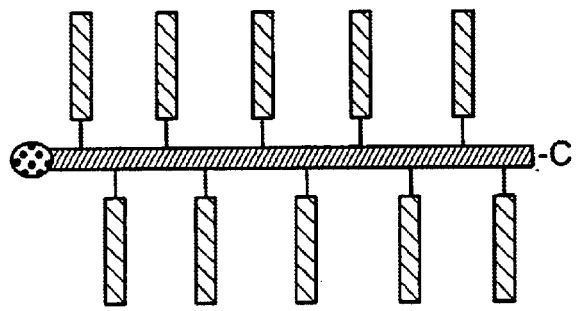
FIGS. 2A–2C are illustrations of intracellular delivery systems of the invention containing a plurality of membrane peptide fusion components attached to a linear peptide.

In order that the present invention may be more-readily understood, certain language is first defined.

The language "intracellular delivery system" is intended to include any combination of components which, when utilized together, facilitate the transport of a selected compound, or "cargo", from a location outside a cell into a location inside a cell. In particular, systems of the invention contain components that bind or otherwise react with the desired cargo, and that facilitate transport of cargo across a biological membrane, for example, a lipid bilayer such as a cellular outer membrane or an episomal vesicular membrane. The systems may also contain a receptor recognition ligand component that binds to a cell surface receptor, as well as other components, such as nuclear localization sequence components and epitope tag components.

The language "cargo" is intended to include any compound intended for intracellular delivery. Examples of types of cargo are drugs, small molecules, proteins, peptides, oligonucleotides, RNA and DNA.

The language "binding component" or "binding peptide component" is intended to include the portion of the intracellular delivery system that binds to cargo. The component can be a peptide containing a chemical entity, a binding motif, which binds to the compound. Preferred components contain a positively charged binding motif. The component can also be a cyclodextrin, e.g., $\beta$-cyclodextrin, containing a binding motif which binds to the compound. Many systems of the invention, particularly those intended for use with large or complex cargo, contain multiple binding peptide components attached to a peptide backbone. The backbone may be linear, branched or circular. The component can be isolated from a naturally occurring protein, or may be a synthetic molecule based in whole or in part on a naturally occurring domain.

The language "backbone" is intended to include a peptide compound to which functional components of intracellular delivery systems of the invention can be covalently attached. The backbone may be linear, branched or circular. Preferred backbones of the invention include at least several charged ionizable or reactive amino acid molecules, e.g., lysine or aspartic acid. A backbone peptide can also contain a single cysteine amino acid residue.

The language "binding motif" is intended to include a chemical entity that binds to a specified target molecule. The binding can be via a covalent bond, an ionic bond, a hydrogen bond or another type of attachment mechanism. The binding motif can be an amino acid, peptide, sugar, lipid, steroid, nucleic acid, small molecule, thiol, anion or cation, or any combination thereof, which binds to the specified target molecule.

The language "membrane fusion component" is intended to include the portion of the intracellular delivery system that facilitates transport of cargo into the cell. The component contains a membrane permeant motif. Preferred membrane fusion components of the systems of the invention are formed of the ANT binding domain and its functional equivalents. The component can be isolated from a naturally occurring protein, or may be a synthetic molecule based in whole or in part on a naturally occurring domain.

The language "receptor recognition ligand component" is intended to include the portion of the intracellular delivery system that directs the system to a particular intracellular location or target cell. The component can bind to a type of cell surface receptor unique to a particular type of cell, or alternatively, the component can bind to a ubiquitous type of cell surface receptor which is present on many cell types. The component can also mimic the function of naturally occurring ligands. The component can be isolated from a naturally occurring protein, or may be a synthetic molecule based in whole or in part on a naturally occurring domain.

The language "nuclear localization sequence component" is intended to include the portion of the intracellular delivery system that facilitates entry of cargo into a cell nucleus.

The language "epitope tag" is intended to include the portion of the intracellular delivery system that can be used to track complexes during intracellular delivery. Preferred epitope tags of the invention are located on the N-terminus of the backbone. Particularly preferred epitope tags are comprised of biotin or an epitope sequence specific to a specific antibody such as anti-Myc.

The language "ANT binding domain motif" is intended to include any isolated protein or peptide containing a functional portion of the amino acid sequence of the ANT binding domain, e.g., an amino acid sequence identical to the sequence of amino acid residues in positions 43–58 in the third helix of the naturally occurring antennepedia protein. That sequence is described as SEQ ID NO: 31 in this application. Such amino acid sequences may be obtained from a natural source, may be chemically synthesized or may be expressed by an encoding nucleic acid.

The language "functional" as applied to a portion or an equivalent of the ANT binding domain motif is intended to include any amino acid sequence or any group of amino acid sequences that can facilitate transport of cargo into a cell at least as effectively as the ANT binding domain motif. Included are sequences which are substantially the same sequence as the ANT binding domain motif. The language "substantially the same sequence" is intended to include sequences which contain a high degree of sequence identity with SEQ ID NO: 31, e.g., sequences which differ by no more than 5, 4, 3, 2 or 1 amino acid residues from SEQ ID NO: 31. The degree of sequence identity between two amino acid sequences can be determined by alignment of the sequences using a computer program, for example, BLAST. The BLAST algorithm relies on several parameters, some of which can be altered. Preferably BLAST is configured as follows: matrix=BLOSUM62; E=1000; W=8 for nucleic acid sequence comparisons or W=3 for amino acid sequence comparisons; strand=both; V =100; B=100; H=1; additional parameters can be set by default. The modifications to the sequence can be conserved or non-conserved, natural and unnatural, amino acids and are preferably outside of the binding domain. Amino acids of the native sequence for substitution, deletion, or conservation can be identified, for example, by a sequence alignment between proteins from related species or other related proteins using BLAST, as described.

Also included are modifications of the structure of the motif, including analogues, derivatives and mimetics, that retain the ability of the motif to facilitate translocation across the lipid bilayer.

The language "analogue" is intended to include compounds in which one or more of the amino acids of the structure of the motif are substituted with a homologous amino acid such that the properties of the original motif are maintained. Particularly included are amino acid sequences which result from conservative amino acid substitutions in the sequence of the ANT binding domain motif. The language "conservative amino acid substitutions" is intended to include amino acids which possess similar side chains (e.g., hydrophobic, hydrophilic, aromatic, etc.), as is known in the art. For example, a first amino acid can be replaced by a second amino acid selected from the group of amino acids with side chains that are similar to the side chain of the first amino acid. Examples of groups of amino acids with similar side chains include nonpolar (alanine, valine, leucine, isoleucine, proline, phenylalanine, tryptophan, methionine, cysteine, glycine); polar(arginine, serine, threonine, tyrosine, lysine, histidine, aspartate, glutamate); aromatic (phenylalanine, tryptophan, tyrosine, histidine); acidic (aspartate, glutamate); basic (lysine, arginine, histidine); nucleophilic (serine, cysteine, threonine). Unnatural amino acids include racemic D, L amino acids, racemic amino acids and other compounds substituted by both amino group (s) and acid group(s). Functional equivalents can be identified by screening the delivery system for activity.

Analytical techniques which compare the ability of a molecule to facilitate translocation across the lipid bilayer with the ability of the ANT binding motif to facilitate translocation across the lipid bilayer can be used to identify molecules which are the functional equivalent of the ANT binding motif. A number of such techniques are known to those of skill in the art. Preferred techniques are those in which the comparative measurement relied upon is directly related to the capability of the tested molecule to facilitate translocation. For example, peptide functional equivalents of the ANT binding motif can be selected using phage display analysis. Phage display techniques are particularly well suited for these types of comparisons due to their ability to screen the properties of large numbers of variants of a protein or peptide. Reagent kits suitable for the screening of functional equivalents of the ANT binding motif are commercially available. One example is the T7 Phage Display system from Novagen, Inc. (Madison, Wis.).

In this method, a library of potentially functionally equivalent sequences are incubated with target cells. Appropriate positive and negative controls are included. Any unbound phage are washed away. Cells are lysed after treatment with trypsin. Then, material which entered the target cells is amplified. The process is repeated until the recovered material can be recovered in sufficient quantity for effective measurement.

The language "derivative" is intended to include compounds in which one or more reaction groups of the compound have been derivatized with a substituent group.

The language "mimetic" or "peptidomimetic" is intended to include compounds in which the chemical structures necessary for the functional activity of the compound have been replaced with other chemical structures which mimic the conformation of the original compound. For example, the peptide backbone can be replaced with a polyvinyl, polyamide or polyester backbone made according to known methods.

The language "small molecule" is intended to include a molecule that is not a direct product of gene transcription or translation, e.g., that is not a protein, RNA or DNA. Such molecules preferably have molecular weights less than about 3kD, most preferably less than about 1.5 KD.

The language "nucleic acid" is intended to include deoxyribonucleic acid (hereinafter "DNA") and ribonucleic acid (hereinafter "RNA"). Both single stranded and double stranded nucleic acids are embraced by this invention, as are higher ordered structures of nucleic acids, for example, RNA that has folded upon its linear strand forming a secondary loop structure and tertiary structure. Nucleic acid sequences encompassed by the present invention can be of any length.

The language "protein" is intended to include any amino acid sequence containing the full-length or substantially the full-length sequence as encoded by the corresponding DNA. Preferably the amino acid sequence contains at least about 90% of the sequence of the residues of the full-length sequence.

The language "peptide" is intended to include any amino acid sequence containing at least two amino acid residues joined by a peptide bond. A peptide derived from a protein is at least one amino acid residue shorter than the amino acid sequence of the full-length protein sequence from which it is derived.

The language "cell" is intended to include not only a particular subject cell but the progeny or potential progeny of such a cell. Because modifications, other than reversions, may occur in succeeding generations, such progeny are characterized by the presence of cargo, yet may not be otherwise identical to the subject cell, but are still included within the scope of the language as it is used herein.

Cells may be prokaryotic, but are preferably eukaryotic, including plant, fungal, insect and mammalian cells. Preferred cells are mammalian, and can be associated with any mammal of interest. Examples include primates, horses, cows, pigs, rabbits, sheep, dogs and cats. Particularly preferred cells are human. Cells of various types can be used including hematopoietic, neural, cutaneous, muscle, epithelial, endothelial, hepatic, kidney, pulmonary, stem, and other precursor and immortalized cells.

The language "subject" is intended to include human and non-human animals. The language "non-human animal" is intended to include all vertebrates and non-vertebrates, e.g., mammals and non-mammals. Examples include fish, primates, horses, cows, pigs, rabbits, sheep, dogs and cats.

Modular Peptide Mediated Intracellular Delivery Systems

One aspect of the invention pertains to intracellular delivery systems. The systems can, to a certain extent, be considered modular, since they are formed of discrete components which perform specific functions (as described above). It should be recognized, however, that in some systems, a component may have multiple functions, while in other systems, there may be considerable functional overlap between the components. Each component is preferably selected such that it optimally performs its specified function when combined with the other components of the system and the cargo intended for intracellular delivery.

It will be recognized that the selection of the components of any particular delivery system may also be influenced by a number of considerations, including the species, system and cell type targeted, and the physiological acceptability of the component. A particularly critical consideration when selecting the components of any system of the invention is the ability to maintain a spatially oriented configuration which facilitates both the optimal attachment of the cargo and its delivery.

In its most basic form, a system of the invention contains a binding peptide component to bind the cargo intended for delivery, and a membrane fusion component to facilitate translocation of the cargo across the cell membrane. Preferably, the components are attached to one another in a linear fashion. In a preferred embodiment, as depicted in FIGS. 1A–1B, the system further contains a receptor recognition binding ligand, to bind to cell surface receptors or otherwise direct the system to a desired location. As illustrated in the figures, the components of the intracellular delivery system can be arranged in any order. A few examples of intracellular delivery systems of the invention are contained in Tables 1 and 2. It will be realized, however, that the systems of the invention are modular in nature. Thus, the components depicted in the tables as being used together can, in many cases, also be used with other components. For example, an FGF receptor recognition ligand component can be used with an HA membrane fusion component, but it can also be used with a Melittin membrane fusion component. Similarly, it can be used with a Histone H2A binding component, or an HMG1 binding component.

TABLE 1

| SEQ ID | Name | Sequence(N->C) Receptor Recognition Ligand/Membrane Fusion/Binding | Residues |
|---|---|---|---|
| SEQ ID NO:1 | DSAP1 | mIL-2(44–60)ligand/WAE fusion/HI DNA binding<br>NYRNLKLPRMLTFKFYLGGWAESLGEALEGGKKSIKKTAKKVKKK | 45 |
| SEQ ID NO:2 | DSAP2 | mIL-2(44–60)ligand/EBO fusion/DNA binding<br>NYRNLKLPRMLTFKFYLGGAIGLAWIPYFGPAAEGGKKKKRKVKK | 45 |
| SEQ ID NO:3 | DSAP3 | mIL-2(73–89)ligand/WAE fusion/H1 DNA binding<br>LEDELGPLRHVLDLTQSGGWAESLGEALEGGKKSIKKTAKKVKKK | 45 |
| SEQ ID NO:4 | DSAP4 | mIL-2(73–89)ligand/EBO fusion/DNA binding<br>LEDELGPLRHVLDLTQSGGAIGLAWIPYFGPAAEGGKKSKKTKKVK | 46 |
| SEQ ID NO:5 | DSAP5 | WAE fusion/mIL-2(44–60)ligand/HI DNA binding<br>WAESLGEALEGGNYRNLKLPRMLTFKFYLGGKKSIKKTAKKVKKK | 45 |
| SEQ ID NO:6 | DSAP6 | WAE fusion/mIL-2(73–89)ligand/HI DNA binding<br>WAESLGEALEGGLEDELGPLRHVLDLTQSGGKKSIKKTAKKVKKK | 45 |
| SEQ ID NO:7 | DSAP7 | EBO fusion/mIL-2(44–60)ligand/DNA binding<br>AAIGLAWIPYFGPAAEGGNYRNLKLPRMLTFKFYLGGKKKKRKVKK | 46 |
| SEQ ID NO:8 | DSAP8 | EBO fusion/mIL-2(73–89)ligand/DNA binding<br>AIGLAWIPYFGPAAEGGLEDELGPLRHVLDLTQSGGKKSKKTKKKK | 46 |
| SEQ ID NO:9 | DSAP9 | WAE fusion/HI DNA binding<br>WAESLGEALEGGKKSIKKTAKKVKKK | 26 |
| SEQ ID NO:10 | DSAP10 | EBO fusion /DNA binding<br>AIGLAWIPYFGPAAEGGKKSKKTKKVK | 27 |
| SEQ ID NO:11 | DSAP11 | mIL-2(73–89)Ligand/WAE fusion<br>LEDELGPLRHVLDLTQSGGWAESLGEALE | 29 |
| SEQ ID NO:12 | DSAP12 | mIL-2(44–60)ligand/EBO fusion<br>NYRNLKLPRMLTFKFYLGGAAIGLAWIPYFGPAAE | 35 |
| SEQ ID NO:13 | DSAP13 | AcN-RPKAKAKAKAKDQTKKKKKRKVKKA | 25 |

TABLE 1-continued

| SEQ ID | Name | Sequence(N->C)<br>Receptor Recognition Ligand/Membrane Fusion/Binding | Residues |
|---|---|---|---|
| SEQ ID NO:14 | DSAP14 | AcN-WAESLGEALEGGKKSIKKTAKKVKKK | 26 |
| SEQ ID NO:15 | DSAP15 | AcN-AIGLAWIPYFGPAAEGGKKSKKTKKVK | 27 |
| SEQ ID NO:16 | TAT | AcN-LGISYGRKKRRQRRRPPQ | 18 |
| SEQ ID NO:17 | NLS | AcN-PKKKRKVEDPY | 11 |
| SEQ ID NO:18 | WAK | AcN-WAKSLGKALKC | 11 |
| SEQ ID NO:19 | EBO | AcN-AAIGLAWIPYFGPAAE | 16 |
| SEQ ID NO:20 | M2 | AcN-EKMSTAISVLLAQAVFLLLTSQR | 23 |
| SEQ ID NO:21 | BindinB18 | AcN-LGLLLRHLRHHSNLLANI | 18 |
| SEQ ID NO:22 | Fertilinβ | AcN-KGEVCRLAQDEADVTEYCNGTSE | 23 |
| SEQ ID NO:23 | Cyritestin | AcN-RGRLCRKSKDQADFPEFCNGETE | 23 |
| SEQ ID NO:24 | DP178 | AcN-YTSLIHSLIEESNQNQQEKNEQELLEDKWASLWNWF | 36 |

TABLE 2

| Receptor<br>Recognition Ligand | Membrane Fusion | Binding |
|---|---|---|
| hGrowth hormone/<br>hGH-receptor | GP120,GP41, TAT(HIV) | Histone H2A |
| hIL1/IL 1-receptor | human parainfluenza virus | Histone H2B |
| FGF/FGF-receptor | HA of Flu virus | Histone H3 |
| TGF-beta/TGFbeta-receptor | Ebola virus | Histone H4 |
| EGF/EGF-receptor | Synthetic | Histone H1/H5 |
| NGF/NGF-receptor | Helical coil-coils | HMG1 |
| Asialoglycoprotein | Alpha hemolysin | RecA |
| Transferrin | GAPDH peptide | Rad51 |
| Insulin/insulin-receptor | Melittin | HU protein |
| X/X-receptors | Hydrophobic segment | Oligolysines |

The components of the system can be connected by a variety of linking compounds. The components can be linked directly or indirectly. Preferred linking compounds are glycine linkers. Alternatively, if the component are peptides, a peptide bond or peptide linker can be utilized.

Figure 4A:
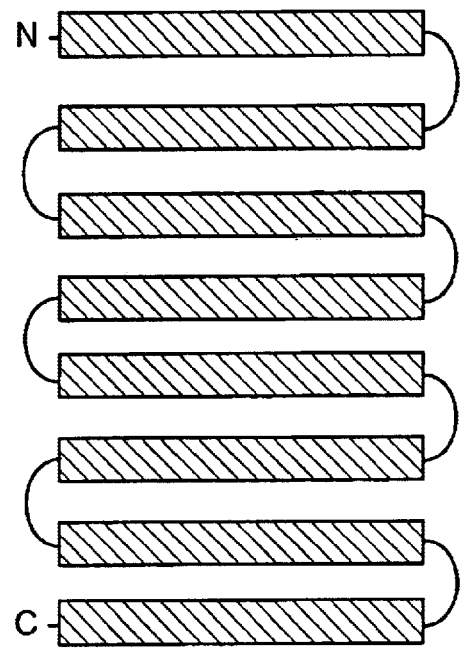
FIGS. 4A–4C are illustrations of alternate configurations of intracellular delivery systems of the invention containing a plurality of membrane peptide fusion components.
Figure 4B:
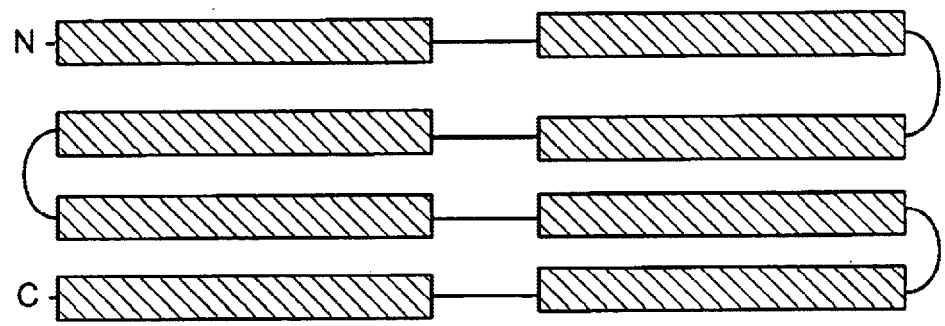
Figure 4C:
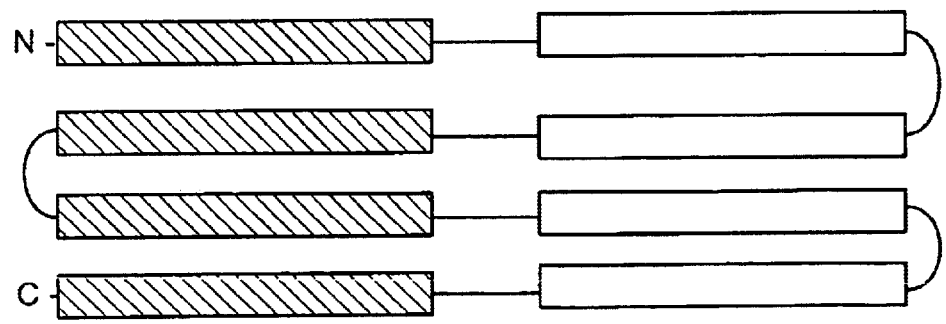
Figure 5:
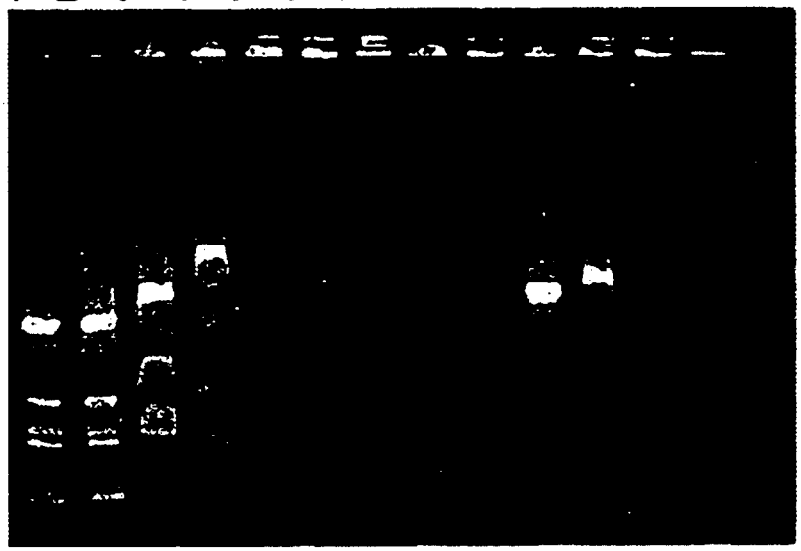
FIG. 5 is a photograph of the results of a gel retardation assay demonstrating the binding of DNA to the binding peptide component in a concentration dependent manner.

In addition, a particular type of linker or a specific linking system can be utilized to configure intracellular delivery systems into a specific form. For example, the amino acids in a series which include a glycine, a serine, an aspartate and a proline amino acid residue are known as a β turn inducing segment. Such segments can be used to connect the components of the intracellular delivery system so that the configuration depicted in FIG. 4A is formed. Other such linking segments are known to those skilled in the art, including those which induce the formation of an α helix and those which induce the formation of a β sheet.

Figure 2B:
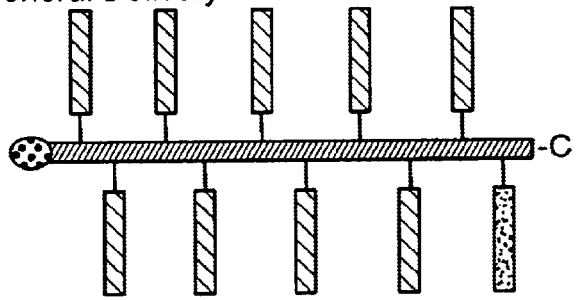
Figure 2C:
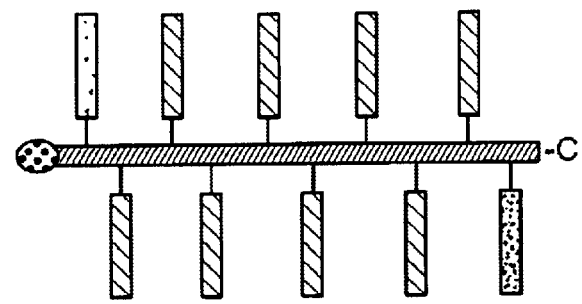

Alternate embodiments of intracellular delivery systems of the invention are depicted in FIGS. 2A–2C. These systems comprise a plurality of membrane peptide fusion components attached to a linear peptide. Preferably the linear peptide component, e.g., the "backbone" component, contains several lysine or aspartic acid amino acid residues. A backbone can also contain a single cysteine amino acid residue. Preferred backbone components contain a preponderance of residues of these type of amino acids, and thus, contain multiple positive or negative charges, e.g., are multivalent. The membrane fusion components are attached via the available reactive centers. For lysine, these are the ε-amino groups.

The physical structure and spatial arrangement of the backbone with its attached components can be a critical aspect of these embodiments. Optimal structures and arrangements can be determined by analyzing the systems in conjunction with cargo components, both prior to and during cargo attachment to the delivery system. For example, for a system intended to deliver DNA cargo, circular dichroism (CD) can be utilized to characterize the individual peptides, the delivery system and the DNA-delivery system complex. Dynamic light scattering can be used to further analyze the complex, and scanning electron microscopy (SEM), atomic force spectroscopy (AFM) and shadow cast transmission electron microscopy (TEM) can be used to characterize the complex in its condensed state.

The peptides can have either homogeneous or heterogeneous functional groups. Homogenous peptides contain functional groups of only one type, while heterogenous peptides include more than one type of peptide sequence. Examples of backbone peptides useful in the systems of the invention are contained in Table 3.

TABLE 3

| SEQ ID | Name | Sequence (EpiTag-N->C-block) | Residues | Available<br>Conjugation<br>Site |
|---|---|---|---|---|
| SEQ ID NO:25 | K20 | KKKKKKKKKKKKKKKKKKKK | 20 | 20 |
| SEQ ID NO:26 | KA20 | KAKAKAKAKAKAKAKAKAKA | 20 | 10 |
| SEQ ID NO:27 | KG20 | KGKGKGKGKGKGKGKGKGKG | 20 | 10 |

TABLE 3-continued

| SEQ ID | Name | Sequence (EpiTag-N→C-block) | Residues | Available Conjugation Site |
|---|---|---|---|---|
| SEQ ID NO:28 | KAA30 | KAAKAAKAAKAAKAAKAAKAAKAAKAAKAA | 30 | 10 |
| SEQ ID NO:29 | KGG30 | KGGKGGKGGKGGKGGKGGKGGKGGKGGKGG | 30 | 10 |
| SEQ ID NO:30 | KPG30 | KPGKPGKPGKPGKPGKPGKPGKPGKPGKPG | 16 | 10 |

A K20 backbone has twenty available side chains, e.g., conjugation sites, that can be linked to functional peptide groups. Ensuring a consistent size for each functional peptide component attached to the array of side chains permits optimal characterization of the spatial arrangement for any specific cargo.

A KA20 backbone has alternating charge and noncharge amino acid residues.

KG20, with ten conjugation sites, is similar in structure to KA20, although with a more flexible backbone due to the achiral nature of the glycine it contains KAA30, with ten conjugation sites, is likely to adopt an a helical structure. (Barbier, B. & Brack, A., 1992, *J Amer Chem Soc* 114:3511–3515; Xiong, H., et al., 1995, *Proc Natl Acad Sci USA* 92:6349–6353; Beasley, J. R. & Hecht, M. H., 1997, *J Bio Chem* 272:2031–2034)

KGG30, with ten conjugation sites, is likely to be very flexible, capable of adopting a variety of structures.

KPG30, with ten conjugation sites, contains proline and glycine residues in addition to lysine.

One residue of aspartic acid can be substituted for one residue of lysine in any of the referenced backbone examples. Such aspartic acid backbones are very structurally versatile which can enhance both placement of cargo and specificity of binding. When preparing such aspartic acid backbones, it is necessary to consider the differences in solubility between lysine and aspartic acid. Moreover, during synthesis, orthogonal blocking groups are likely to be required.

A. Binding Peptide Component

Many proteins and peptides contain chemical motifs that bind to other compounds, both selectively and specifically. For example, it is generally recognized that peptides containing clusters of lysine and arginine bind nucleic acids. (Harrison S., 1991, *Nature* 353:715–719). Therefore, peptides containing such clusters can be selected when the cargo is a nucleic acid. When the nucleic acid is DNA, a binding peptide motif which binds to DNA with less specificity is selected, so that the system can be utilized with a wide range of DNA sequences. Histones have very little DNA binding selectivity, and their binding domains are rich in positively charged lysine and arginine residues that interact with the negatively charged DNA phosphodiester backbones. (Baxevanis, A. D. & Landsman, D.,1998, *Nuc Acids Res* 26:373–375) For that reason, when the cargo is DNA, preferred binding peptide components are those which contain binding motifs such as those derived from chromosomol proteins of the histone family, for example, Histone H1, Histone H2A, Histone H2B, Histone H3, Histone H4 and Histone H5. A particularly preferred binding peptide component for DNA intracellular delivery systems is one that contains a portion of the binding domain motif of the human histone H1 protein. Examples of other preferred binding peptide components are HMG1, RecA, Rad51, HU protein and oligolysines.

It is also appropriate, however, to select a binding motif which binds to DNA with more specificity when such enhanced binding is advantageous.

The overall length of the component can be important in selecting the binding peptide component. Preferred peptides for binding components for systems with DNA cargo are those which are small enough so that the DNA cargo can be readily disassociated in the cell nucleus, so that the efficiency of expression is not compromised. A preferred length for the binding peptide component is less than about 200 amino acid residues, a particularly preferred length is about 5, 10, 15, 20 or 25 amino acid residues.

The ability of any particular peptide to bind with a cargo compound at a specific concentration can be experimentally determined. Binding activity and the affinity of the cargo for the binding motif can be determined using gel retardation assays, gel filtration, ultraviolet (UV) spectroscopy and BIAcore. These methods measure the characteristics of the complex formed by the attachment of the binding motif to the cargo in different ways. A band shift assay using non-denaturing agarose gel electrophoresis can ascertain the extent of complex formation, while gel filtration can determine the size range of the complex. A UV spectroscopic assay can measure the extent to which cargo is condensed. BIAcore can analyze association/disassociation constants. Using the results from a relevant set of such experiments, one skilled in the art can select particular peptide binding components to optimally bind any specific cargo.

For example, peptides in various amounts can be incubated with DNA to allow formation of DNA-peptide complexes. Agarose/ethidium bromide gel electrophoresis can be used to ascertain the formation of DNA-peptide complexes. Similarly, the complex can be analyzed by gel filtration of different size resins and columns to determine a range of molecular weights. Each complex can be examined via UV spectroscopy to determine the amount of naked DNA, and a quantitative binding constant for each can be obtained using the BIAcore measurement. The peptides can be immobilized on the streptavidin BIAcore chip with biotinylated peptides. The binding of DNA with the peptide can be quantitatively measured by flowing DNA over the peptide modified surface.

The complex can also be subjected to digestion using several specific restriction endonucleases or DNase I to determine the integrity of the DNA at various incubation time intervals. In such experiments, aliquots of reactions can be removed at various times and the reaction stopped by addition of EDTA. The sample can be analyzed using gel electrophoresis.

In some embodiments, the binding component can be a cyclodextrin, most preferably a β cyclodextrin. Cyclodextrins are cycloamyloses suitable for use as non-toxic carrier molecules. In addition, the cavity size of , cyclodextrin is the right size and character to carry many hydrophobic small molecules. Thus, cyclodextrins can be appended to delivery systems in order to deliver small molecules, drugs, and other therapeutic and marker molecules. The primary alcohols of the cyclodextrin ring can be specifically oxidized using TEMPO-mediated oxidation (Nooy, A. E. J. et al *Carb. Res.* 1995 269:89–98). This oxidation procedure generates carboxylic acids from primary alcohols. These reactive centers can then react with the α-amino structure contained in certain receptor recognition ligand components using dicyclohexycarbodiimide, or other more efficient condensing agents so that the components are linked in positions outside the ring.

B. Membrane Fusion Peptide Component

A number of proteins contain membrane internalization motifs. Some are viral in origin while others are found in membrane proteins or membrane fusogenic proteins such as toxins and sperm-egg fusion proteins. (Hernandez, L. D., et al. 1996, *Ann Rev Cell Dev Biol*; Durell, S. R., et al., 1998, *Mol Membr Biol* 14:97–112).

Preferred membrane fusion components, those which most readily facilitate membrane translocation, in general, have several clusters of positively charged amino acids and are spaced with hydrophobic residues, particularly tryptophan, tyrosine, and phenylalanine, aromatic residues and, to a lesser extent, leucine, isoleucine, valine, proline, methionine, glutamine, asparagine and alanine. While not wishing to be bound by hypothesis, it is believed that the positively charged residues bring the cargo to the negatively charged cell membrane surface. Then the aromatic and others residues facilitate the translocation.

Many preferred membrane fusion components comprise a binding domain motif from a homeodomain protein able to facilitate translocation across biological membranes, for example, lipid bilayers such as cell outer membranes and endosomal vesicular membranes. Particularly preferred membrane fusion components comprise the ANT binding domain motif originally derived from the third helix of the *Drosophila* protein, *antennapedia*, or its functional equivalent. The ANT binding domain motif is considered to be an amino acid sequence identical to the sequence of amino acid residues in positions 43–58 in the third helix of the naturally occurring *antennapedia* protein. (Derossi, D., et al. 1998, *Trends Cell Bio* 8:84–87)

Functional equivalents of the ANT binding domain include any amino acid sequence or any group of amino acid sequences that can facilitate transport of cargo into a cell at least as effectively as the ANT binding domain motif. Sequences which are substantially the same sequence as the ANT binding domain motif are included, as are modifications of the structure of the motif, including analogues, derivatives and mimetics, as long as the ability of the motif to facilitate translocation across the lipid bilayer is retained.

A peptide in which the sequence of the amino acid residues is directly reversed from the sequence of the amino acid residues in the naturally occurring protein is considered within the scope of the invention. In this reverse order peptide, the amino acid sequence of the peptide is identical to the amino acid sequence of positions 58–43 of the naturally occurring protein. Moreover, motifs may be composed of either L or D amino acid enantiomers.

C. Receptor Recognition Ligand Component

Many cell ligand and receptor pairs are known, and their interactions are well characterized, including those of several types of growth factors, FGF2, FGF7, EGF, PDGF, transferrin, human growth hormone and IL2 all of which can be utilized for receptor mediated compound delivery.

In one embodiment, the binding motif of a receptor recognition ligand component is selected to pair with a cell receptor unique to the surface of a particular type of cell. In this manner, the intracellular delivery system can be specifically directed to deliver its cargo to that particular type of cell. In an alternate embodiment, the binding motif of a receptor recognition ligand component is selected to pair with a ubiquitous cell receptor, e.g, one that is contained on the surface of several types of cells. Such systems are useful for generalized delivery of cargo to a range of cells.

Thus, particular binding motifs can be selected for incorporation into the receptor recognition ligand components of the delivery systems of the invention based on the cell selected for delivery or the type of delivery desired. The binding motif for the receptor recognition ligand component can be identified or its identity can be confirmed by manufacturing various fragments of the selected cell receptor extracellular domain and screening them for their ability to bind.

Information relating to useful binding motifs for systems of the invention can be obtained from many sources. (Wu, G. Y. & Wu, C. H., 1987, *J Biol Chem* 262:4429–4432; Cotten, M. et al., 1993, *Proc Natl Acad Sci USA* 89:6094–6098; Kasahara, N. et al., 1994, *Science* 266:1373–1377; Chen, J. et al., 1994; *FEBS Letters* 338:167–169; Shmizu, N. et al., 1994, *Cancer Gene Ther* 3:113–120; Hashida, M. et al., 1998, *J Controlled Release* (5)3:301–310; Hoganson, D. K. et al., 1998, *Hum Gene Ther* 9:2565–2575; Plank, E. et al., 1997, *J Biol Chem* 269:12918–12924; Larocca, D. et al., 1999, *FASEB J* (1) 3:727–734) Furthermore, the molecular structures of known ligand proteins can be obtained from the Protein Data Base (PDB).

Preferred motifs are derived from FGF2, FGF7, human growth hormone, and interleukin2 (IL2). (Zurawski, S. et al.,1993, *EMBO J* 8:2583–2590)

In an alternate embodiment, the binding motif of a receptor recognition ligand component is selected such that it has some affinity for a cell surface or a cell component. The binding motifs of such components may not directly correspond to a cell receptor and may not be derived from the ligand which naturally pairs to a cell receptor. Rather, targeting to a particular cell can be accomplished by the use of trafficking sequences, for example, galactose or the asialoglycoprotein liver receptor. The binding motifs may, however, mimic the function of a naturally occurring ligand. Thus, peptide ligand mimetics such as RGD for integrins and CNRCGG for tumor vasculature can be used to direct

TABLE 4

| | | |
|---|---|---|
| SEQ ID NO:31 | 43-58 | Arg-Gln-Ile-Lys-Ile-Trp-Phe-Gln-Asn-Arg-Arg-Met-Lys-Trp-Lys-Lys |
| SEQ ID NO:32 | 58-43 | Lys-Lys-Trp-Lys-Met-Arg-Arg-Asn-Gln-Phe-Trp-Ile-Lys-Ile-Gln-Arg |
| SEQ ID NO:33 | D43-58 | Arg-Gln-Ile-Lys-Ile-Trp-Phe-Gln-Asn-Arg-Arg-Met-Lys-Trp-Lys-Lys |
| SEQ ID NO:34 | Pro50 | Arg-Gln-Ile-Lys-Ile-Trp-Phe-Pro-Asn-Arg-Arg-Met-Lys-Trp-Lys-Lys |
| SEQ ID NO:35 | 3Pro | Arg-Gln-Pro-Lys-Ile-Trp-Phe-Pro-Asn-Arg-Arg-Lys-Pro-Trp-Lys-Lys |
| SEQ ID NO:36 | Phe48,56 | Arg-Gln-Ile-Lys-Ile-Phe-Phe-Gln-Asn-Arg-Arg-Met-Lys-Phe-Lys-Lys |
| SEQ ID NO:37 | Met-Arg | Arg-Gln-Ile-Lys-Ile-Trp-Phe-Gln-Asn-Met-Arg-Arg-Lys-Trp-Lys-Lys |
| SEQ ID NO:38 | 7Arg | Arg-Gln-Ile-Arg-Ile-Trp-Phe-Gln-Asn-Arg-Arg-Met-Arg-Trp-Arg-Arg |
| SEQ ID NO:39 | W/R | Arg-Arg-Trp-Arg-Arg-Trp-Trp-Arg-Arg-Trp-Trp-Arg-Arg-Trp-Arg-Arg | the trafficking of cargo into target cells. Such systems are useful in conjunction with cargo that allows visual magnetic resonance imaging (MRI) applications, for example, to detect tumors.

Some examples of alternate receptor recognition ligands, some of which include biological effectors as cargo, are contained in Table 5.

TABLE 5

| SEQ ID NO | Receptor Recognition Ligand/Cargo | Target/Function |
|---|---|---|
| SEQ ID NO:40 | -CGFECVRQCPERC- | Mouse lung vasculature targeting (Correction of CF) |
| SEQ ID NO:41 | CNRCGG$_D$(KLAKLAKKLAKLAK) Targeting Apoptotic | Tumor Endothelium/ proapoptotic |
| SEQ ID NO:42 | -MAGPHPVIVITGPHEE- | Inhibitor of NFAT (immuno-modulator) |
| SEQ ID NO:43 | -PKKKRKV- | Transport, sequence-specific DNA-binding and nuclear localization |
| SEQ ID NO:44 & SEQ ID NO:45 | -RQVFQVAYIIIKA & YIGSR- | Lamanin 1 binding (neural cell adhesion) |
|  | HC fragment of tetanus toxin | Neuronal targeting |

II. Manufacturing Modular Peptide Mediated Intracellular Delivery Systems

The intracellular delivery systems of the invention are very versatile, due in large part to their modular nature, e.g., due to the fact that the systems are comprised of individual components, each of which is selected to optimally contribute to a particular aspect of the intracellular delivery process. Thus, systems can be specifically tailored to facilitate delivery of any particular target in any particular way.

In general, the components of the intracellular systems are manufactured separately and subsequently attached to one another. The components can be manufactured according to methods generally known in the art. For example, the components can be manufactured employing known organic synthesis methods. The preferred peptide components can be synthesized by F-moc solid phase chemistry using an automated peptide synthesizer such as a Rainin PS3 (Woburn, Mass.). The synthesis can also be accomplished using T-boc chemistry. Commercial laboratories, such as the one operated by Research Genetics (Huntsville, Ala.) can provide peptides suitable for use in the systems of the invention in considerable quantities. In carrying out the synthesis, derivation or inactivation of any group required for proper functioning of the particular component should be avoided. Appropriate syntheses are highly dependent upon the chemical nature of the binding motif and, generally, can be selected from an advanced organic chemistry text, such as March, et a. Advanced Organic Chemistry, 3rd Edition (1985) John E. Wiley & Sons, Inc., New York, N.Y., or other known methods.

Following synthesis, components can be purified by high-performance liquid chromotography (HPLC) methods known in the art. Characterization of the peptides can be accomplished by use of mass spectrography and amino acid composition analysis. Moreover, the structures of synthesized peptides can be ascertained by circular dichroism (CD) and nuclear magnetic reasonance (NMR) under appropriate conditions.

The synthesized components can be connected to one another by a variety of linking compounds. The components can be linked directly or indirectly. Preferred linking compounds are glycine linkers.

For example, a delivery system of the invention can be manufactured by reacting a plurality of membrane fusion components to a poly-L-lysine backbone. The activated carboxyl group on the C-terminus of the branched linking peptide can be crosslinked to the epsilon N of the lysine side chain of the backbone. The side chains of the linking peptide do not require deprotection after synthesis, but the N-terminus should be acetylated to avoid undesired reactions. After activation, the poly-L-lysine can be added to the reaction and allowed to react for about 12 hours. The linked multivalent peptides can be purified through a C18 cartridge and freeze dried. The side chains of the linking peptide can then be deprotected and purified. Samples can be freeze dried, dissolved in water, sterile filtered and then utilized for intracellular delivery.

In addition, a particular type of linker or a specific linking system can be utilized to configure intracellular delivery systems into a specific form. For example, the amino acids in a series which include a glycine, a serine, an aspartate and a proline amino acid residue are known as a β turn inducing segment. Such segments can be used to connect the components of the intracellular delivery system so that it forms the configuration depicted in FIG. 4A. Other such linking segments are known to those skilled in the art including those which induce the formation of an a helix and those which induce the formation of a β sheet.

Alternatively, particularly when the intracellular delivery system is one with a more basic configuration, for example, those systems depicted in FIGS. 4A–4C, and the components are peptides, it is possible to form a conjugate or a fusion protein manufactured according to known methods. Where a fusion protein is desired, the molecule can be manufactured according to known methods of recombinant DNA technology. For example, the fusion protein can be expressed by a cell containing a plasmid comprising sequences which code for the various components. In this type of system, a peptide bond can be utilized.

III. Methods of Utilizing Modular Peptide Mediated Intracellular Delivery Systems A further aspect of the invention relates to a method of delivering a compound, cargo, particularly DNA cargo, into a cell utilizing an intracellular delivery system of the invention. In a preferred embodiment of this method, the cargo is a therapeutic compound which is delivered into a cell for use in a subject. In a preferred embodiment, the cargo is DNA under the functional control of the regulatory elements necessary for expression. Such elements can be those associated with the DNA in its natural state or any other regulatory elements which can control or regulate expression in an appropriate manner. The elements can be isolated from a naturally occurring source, or may be a synthetic molecule based in whole or in part on a naturally occurring element. In a particularly preferred embodiment, the cargo is the DNA under the functional control of its naturally occurring regulatory elements. In a particularly preferred embodiment, subsequent to the delivery of the therapeutic cargo, the cell is used in gene therapy.

While not wishing to be bound by hypothesis, it is likely that delivery of the cargo occurs via one of the two pathways generally described in the following paragraphs. It is also possible that delivery occurs via a combination of the steps of the two pathways, or yet another pathway.

In one pathway, the cargo is attached to the binding peptide component via the binding motif contained in the component so that a complex is formed between the intracellular delivery system and the cargo. The complex binds to the cell surface due, at least in part, to the difference in electrical charge between the complex and the cell surface. The receptor recognition ligand component directs the complex to a cell surface receptor. Certain receptor recognition ligand components target particular cells via receptors unique to those cells, while others target ubiquitous receptors such as transferrin or integrin. The complexed system enters the cell through receptor-mediated endocytosis. The translocation is likely also facilitated by the membrane fusion peptide component of the system. The complex enters an endosome. A portion of the complex escapes from the endosome into the cytoplasm and makes its way to the nucleus. As was the case when the complex translocated across the cell membrane, it is likely that the translocation of the complex from the endosome is facilitated by the membrane fusion peptide component of the system. Some disassociation of the cargo from the delivery system may occur in the endosome. A portion of the cargo reaches the nucleus where transcription can occur.

In an alternative pathway, the cargo is attached to the binding peptide component via the binding motif contained in the component so that a complex is formed between the intracellular delivery system and the cargo. The binding domain motif of the membrane fusion component then associates directly with the cell membrane, partly due to electrostatic interactions between the positive charges of the basic amino acids and the negative charges carried by the membrane lipid or sugar components. This association is stable enough to allow an accumulation at the water-membrane interface and to destabilize the membrane organization from a lipid bilayer to an inverted micelle. The cargo is subsequently released into the cytoplasm where a portion reaches the nucleus where transcription can occur.

The methods of the invention can be used on cells in culture, e.g., in vivo or ex vivo. For example, cells can be cultured in vitro in culture medium and the step of introducing the cargo-delivery system complex to the surface of the cell can be effected by adding the cargo-delivery system to the culture medium.

The integrity of the complex in tissue culture media can be determined by incubating samples in the absence and presence of nuclease and various proteases at different concentrations and at various time periods. Moreover, the results obtained using systems containing receptor recognition ligand components and membrane peptide fusion components, systems containing only membrane peptide fusion components, and systems containing only receptor recognition ligand components in various assays can be compared to assess the selectivity and efficiency of any particular system. Delivery of the systems into cells lacking the corresponding cell surface receptor can be utilized as a control. Moreover, the efficiency of delivery can be analyzed using methods including Northern and Southern blotting including in situ hybridization, immunochemistry and Western blotting. Plasmids containing the gene for green fluorescent protein (GFP) or its derivatives (EGFP, EBFP, YFP) under control of a constitutive reporter promoter for GFP expression can be used to determine the capability of a particular system to deliver a DNA cargo into target cells. FACS can be used to determine the efficiency of the delivery. To measure the efficiency of an intracellular delivery system intended to deliver non-DNA cargo, for example, a system such as that depicted in FIG. 1A or 1B, the green fluorescent protein can be attached to the C terminal end of the delivery system, so that a fluorescent measurement of the protein translocated into the cell can be performed. Luciferase and β-galactosidase reporter genes can also be used in these assays.

For example, to assess the delivery of a DNA-cargo delivery system complex into cells contained in tissue culture, the complex can be incubated in cell culture containing the backbone with receptor recognition ligand components but without binding peptide components. Similarly, IL2 protein can also be used to determine the efficiency of receptor mediated DNA delivery. In this assay, the free ligands compete for the IL2 receptor on the cell surface, making reduction of GFP expression likely. Results from the same assays conducted on cells without, or with reduced numbers of, IL2 receptors can be compared to determine the efficiency of DNA delivery in different cell lines.

Alternatively, a peptide can be detectably labeled in a unique position and confocal microscopy can be used to monitor cell entry and trafficking directly.

The transfected cells can be grown in culture and introduced into a subject in a variety of ways. Cells may be administered by injection into the vascular system. The cells may be applied as a graft. Cells may also be encapsulated prior to implantation into the subject. In each case, the number of cells employed can be determined by the skilled artisan depending upon a number of criteria. Such criteria include the therapeutic purpose for the treatment, the anticipated life span of the cells, the general protocol to be used including, for example, the number of required administrations, the ability of the cells to multiply and the like.

Alternatively, the method can be performed on cells present in a subject, e.g., as part of an in vivo therapeutic protocol. For in vivo methods, the cell is preferably found in a subject and the step of introducing the cargo-delivery system complex to the surface of the cell is effected by administering the cargo-delivery system to the subject. Such administration will generally be by injection, e.g., intravascularly or intramuscularly, by inhalation, or another parenteral mode. As in the ex vivo therapies, criteria can be applied to determine the amount and frequency of any therapeutic cargo which should be optimally employed.

Alternatively, the initial delivery of the cargo can be more limited with introduction into the subject being quite localized. For example, the delivery system can be introduced via an indwelling medical device such as an endovascular stent or catheter. In this method, the complex is attached to the medical device, either covalently or non-covalently. When attached covalently, an anchorage tail and a timed release scissile bond are both included in the attachment complex. Some time after placement of the device in the subject, for example, post-angioplasty, the timed released scissle bond can break, resulting in local delivery of the cargo.

Local delivery of many therapeutic compounds is extremely advantageous. Such localized delivery can result not only in targeted delivery of a desired therapeutic compound, but can also prevent the systemic effects often associated with other modes of delivery. Such delivery can be used to treat the restenosis so endemic to the placement of vascular stents by making locally available substances that inhibit smooth muscle cell overgrowth. In addition, many alleles and small molecules are good candidates for localized delivery. For example, dominant negative forms of cMYB, PCNA1 and other such compounds as well as inhibitory peptide motifs can be used to turn off the proliferative signals in targeted smooth muscle cells. The gene for thymidine kinase (Tk) can be delivered locally to sensitize the newly proliferating smooth muscle cells to gangcyclovir treatment.

The invention is further illustrated by the following non-limiting examples. The contents of all the patents, patent applications and other references cited are hereby expressly incorporated by reference in their entireties.

EXEMPLIFICATION

EXAMPLE 1

Preparation of Multivalent Modular Synthetic Peptide

Some ANT peptides were synthesized by activating the COOH terminus of the blocked ANT, then reacting the ε-amino group on the lysine containing peptide using carbodiimide/imidazole. After the coupling reaction was complete, the blocking groups were removed with trifluoroacetic acid. The peptide reagent was further treated by precipitation and lyophilization, diluted in water, and then sterile filtered. Typical yield of one reaction was 1–2 mg peptide. Peptides were also crosslinked with poly-L-lysine (Sigma, average size 47).

EXAMPLE 2

Gene Delivery in Cell Cultures

Experiments were carried out in human umbilical vein endothelial cells (HUVEC), human pulmonary arterial endothelial cells (HPAEC), COS-7 cells, NIH-3T3 cells, CHOK1 cells and HEK293T cells which include standard, primary and immortalized cells. The plasmid containing the enhanced green fluorescent protein (pEGFP-C1, Clontech, CA) was used as the monitor marker. For the positive control, Superfect™ (Qiagen, CA) was used. Superfect™ is an activated dendrimer with multiple branches. DNA wraps around Superfect™ molecules, thus condensing DNA in a similar manner to that of histones in eukaryotic nuclei. For negative controls, cells were exposed to naked DNA alone and DNA incubated with poly-L-lysine.

DNA-peptide complexes were made by incubating the DNA and delivery peptide in 100.0 µl of serum free DMEM or sterile water+about 10–15 µg of peptide+2.0 µg of DNA for 1–2 hours. The growth media was removed from the target cell and washed IX with 1XPBS. The 130.0 µl of peptide-DNA complex was pipetted onto each well of a cluster 6 plate and incubated for 15 minutes at 37° C. After this incubation, 1.0 ml of fresh low-protein-DMEM containing 1% NuSerum (Becton-Dickinson) medium was added to each well and the plates incubated a further 12–48 hours. Then, fresh media with DMEM/10% FBS was added to the cell culture and incubated further before fluorescence microscopy to assess GFP expression. The expression level of GFP was examined under a fluorescent microscope, and GFP positive cells were assessed for its % of green cells and the intensity of the green fluorescent signal. FACS analysis of the transfected cell populations revealed that depending on the cell type between 1–20% of the cells were transfected with the peptide conjugate and between 50 and 80% were transfected with DNA-Superfect™. About 1% of primary human cells were transfected, while about 20% of COS-7 cells were transfected.

Figure 6:
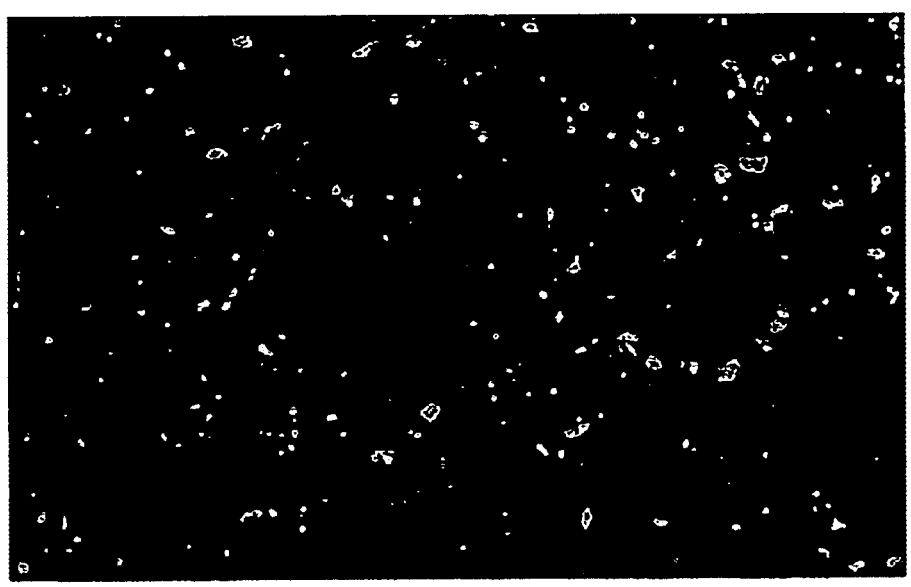
FIG. 6 is a photograph of COS-7 cells transfected by a delivery system of the invention.

Qualitative and quantitative results suggest that the multivalent synthetic peptide system can perform high efficiency gene delivery with no apparent cytotoxicity. A representative example of the results of these experiments is demonstrated in FIG. 6. In all experiments, no chloroquine was used.

Equivalents

While this invention has been particularly shown and described with references to preferred embodiments thereof, it will be understood by those skilled in the art that various changes in form and details may be made therein without departing from the scope of the invention encompassed by the appended claims. Those skilled in the art will recognize or be able to ascertain using no more than routine experimentation, many equivalents to the to the embodiments of the invention described specifically herein. Such equivalents are intended to be encompassed by the scope of the claims.

What is claimed is:

1. An intracellular delivery system comprising:
   a. a binding peptide component;
   b. a membrane fusion peptide component, selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO: 39; and
   c. DNA comprising a coding region under functional control of a promoter, wherein each component is attached to a backbone comprising a plurality of amino acid molecules selected from the group of lysine and aspartic acid amino acid molecules.

2. An intracellular delivery system comprising:
   a. a binding peptide component;
   b. a membrane fusion peptide component, selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO: 39;
   c. DNA comprising a coding region under functional control of a promoter; and
   d. a receptor recognition ligand component, wherein each component is attached to a backbone comprising a plurality of amino acid molecules selected from the group of lysine and aspartic acid amino acid molecules.

3. The system of claim 1, wherein the DNA comprises a coding region under functional control of its naturally occurring promoter.

4. An intracellular delivery system comprising:
   a. a plurality of membrane fusion peptide components selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO: 39;
   b. DNA comprising a coding region under functional control of a regulatory element; and
   c. a plurality of peptide binding components, wherein each component is attached to a backbone comprising a plurality of amino acid molecules selected from the group of lysine and aspartic acid amino acid molecules.

5. The system of claim 4 further comprising a receptor recognition ligand component.

6. The system of claim 4, wherein the DNA comprises a coding region under functional control of its naturally occurring regulatory elements.

7. A method of delivering DNA comprising a coding region under functional control of a regulatory element into a cell in vitro comprising:
   a. attaching the DNA comprising a coding region under functional control of a regulatory element to an intracellular delivery system comprising;

1. a binding peptide component; and
2. a membrane fusion peptide component selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO:39 under conditions suitable for formation of a cargo-delivery system complex,
   wherein each component is attached to a backbone comprising a plurality of amino acid molecules selected from the group of lysine and aspartic acid amino acid molecules;
b. introducing the cargo-delivery system complex to the surface of a cell, under conditions suitable for delivery of the complex into the cell; and
c. delivering the complex in vitro.

8. The method of claim 7, wherein the DNA comprises a coding region under functional control of its naturally occurring regulatory elements.

9. The method of claim 7, further comprising a step of utilizing the cell in gene therapy.

10. The system of claim 2, wherein the DNA comprises a coding region under functional control of its naturally occurring promoter.

11. A method of delivering DNA comprising a coding region under functional control of a regulatory element into a cell in vitro comprising:
   a. attaching the DNA comprising a coding region under functional control of a regulatory element to an intracellular delivery system comprising:
      1. a binding peptide component;
      2. a membrane fusion peptide component selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO:39 under conditions suitable for formation of a cargo-delivery system complex; and
      3. a receptor recognition ligand component,
      wherein each component is attached to a backbone comprising a plurality of amino acid molecules selected from the group of lysine and aspartic acid amino acid molecules;
   b. introducing the cargo-delivery system complex to the surface of a cell, under conditions suitable for delivery of the complex into the cell; and
   c. delivering the complex in vitro.

12. The method of claim 11, wherein the DNA comprises a coding region under functional control of its naturally occurring regulatory elements.

13. The method of claim 11, further comprising a step of utilizing the cell in gene therapy.

14. A method of delivering DNA comprising a coding region under functional control of a regulatory element into a cell in vitro comprising:
   a. attaching the DNA comprising a coding region under functional control of a regulatory element to an intracellular delivery system comprising:
      1. a plurality of peptide binding components; and
      2. a plurality of membrane fusion peptide components selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO: 39 under conditions suitable for formation of a cargo-delivery system complex,
      wherein each component is attached to a backbone comprising a plurality of amino acid molecules selected from the group of lysine and aspartic acid molecules;
   b. introducing the cargo-delivery system complex to the surface of a cell, under conditions suitable for delivery of the complex into the cell; and
   c. delivering the complex in vitro.

15. The method of claim 14, further comprising a receptor recognition ligand component.

16. The method of claim 14, wherein the DNA comprises a coding region under functional control of its naturally occurring regulatory elements.

17. The method of claim 14, further comprising a step of utilizing the cell in gene therapy.

* * * * *